United States Patent
Jocke et al.

(10) Patent No.: US 9,262,785 B1
(45) Date of Patent: Feb. 16, 2016

(54) AUTOMATED BANKING MACHINE IN COMMUNICATION WITH A REMOTE COMPUTER THAT GENERATES AN ALERT MESSAGE WHEN A CALCULATED NUMBER OF TRANSACTIONS EXCEEDS A THRESHOLD

(71) Applicants: Ralph E. Jocke, Medina, OH (US);
Patricia A. Walker, Medina, OH (US);
Daniel D. Wasil, Wellington, OH (US)

(72) Inventors: Ralph E. Jocke, Medina, OH (US);
Patricia A. Walker, Medina, OH (US);
Daniel D. Wasil, Wellington, OH (US)

( * ) Notice: Subject to any disclaimer, the term of this patent is extended or adjusted under 35 U.S.C. 154(b) by 3 days.

(21) Appl. No.: 14/273,991

(22) Filed: May 9, 2014

Related U.S. Application Data

(60) Provisional application No. 61/862,696, filed on Aug. 6, 2013, provisional application No. 61/925,393, filed on Jan. 9, 2014.

(51) Int. Cl.
| | | |
|---|---|---|
| *G06Q 40/02* | (2012.01) | |
| *G06Q 20/10* | (2012.01) | |
| *G07F 19/00* | (2006.01) | |

(52) U.S. Cl.
CPC .......... *G06Q 40/02* (2013.01); *G06Q 20/1085* (2013.01); *G07F 19/203* (2013.01)

(58) Field of Classification Search
CPC .......... G07D 11/0021; G07D 2211/00; G07F 19/20; G07F 19/201; G07F 19/203; G07F 19/206; G07F 19/209; G07F 19/211; G06Q 20/1085
USPC ......... 235/379; 705/43; 194/205–207; 902/8, 902/14, 17, 18, 20, 21
See application file for complete search history.

(56) References Cited

U.S. PATENT DOCUMENTS

| | | | |
|---|---|---|---|
| 8,690,052 B1 * | 4/2014 | Lewis et al. | 235/379 |
| 2006/0049256 A1 * | 3/2006 | von Mueller et al. | 235/449 |
| 2008/0265018 A1 * | 10/2008 | Kemper et al. | 235/379 |
| 2010/0059587 A1 * | 3/2010 | Miller et al. | 235/379 |
| 2011/0016052 A1 * | 1/2011 | Scragg | 705/44 |
| 2011/0246278 A1 * | 10/2011 | Kubo | 705/14.25 |
| 2014/0207673 A1 * | 7/2014 | Jeffries et al. | 705/43 |

\* cited by examiner

*Primary Examiner* — Michael G Lee
*Assistant Examiner* — Suezu Ellis
(74) *Attorney, Agent, or Firm* — Walker & Jocke

(57) ABSTRACT

An automated banking machine operates to cause financial transfers responsive at least in part to data read from data bearing records. The automated banking machine is operative to communicate with at least one remote computer that generates an alert message when a calculated number of transactions on a particular account exceeds a threshold.

20 Claims, 25 Drawing Sheets

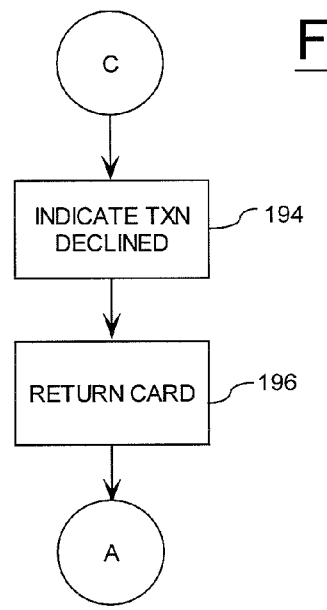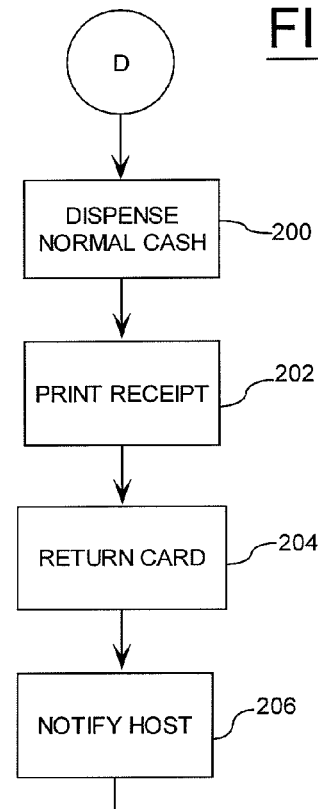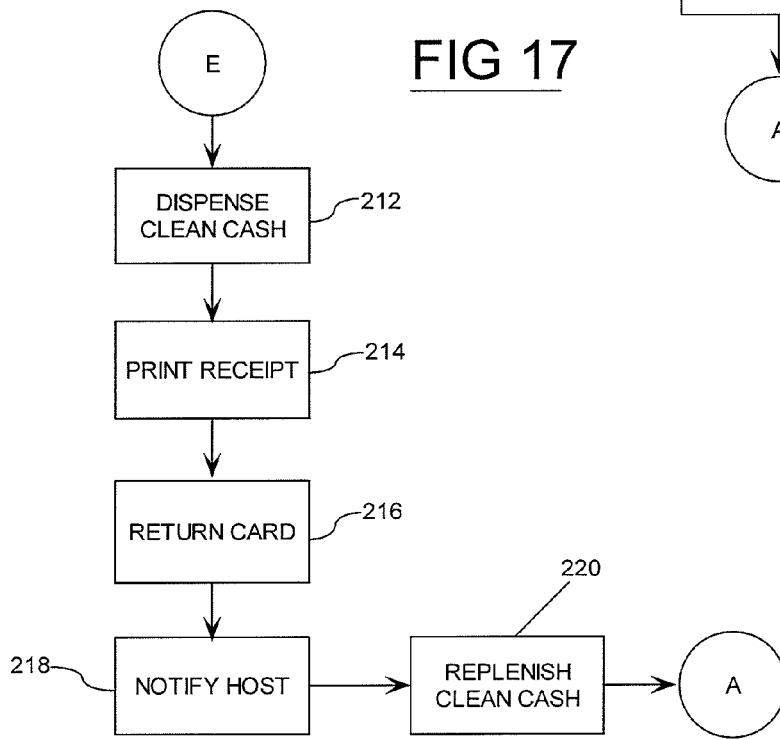

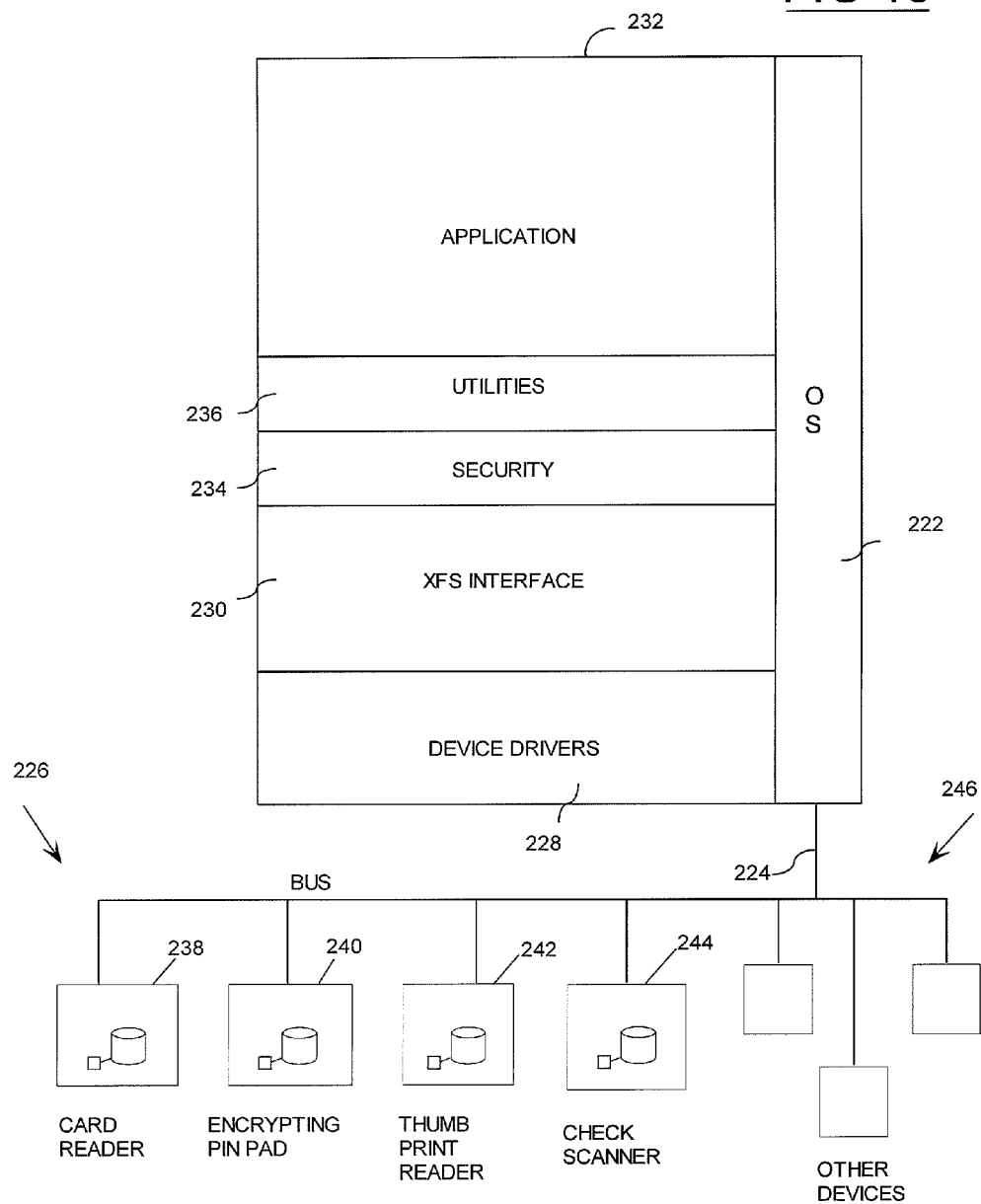

AUTOMATED BANKING MACHINE IN COMMUNICATION WITH A REMOTE COMPUTER THAT GENERATES AN ALERT MESSAGE WHEN A CALCULATED NUMBER OF TRANSACTIONS EXCEEDS A THRESHOLD

TECHNICAL FIELD

This invention pertains to automated banking machines that are controlled responsive to data read from data bearing records such as user cards, which may be classified in U.S. Class 235, Subclass 379.

BACKGROUND

Automated banking machines may include a card reader that operates to read data from a bearer record such as a user card. The automated banking machine may operate to cause the data read from the card to be compared with other computer stored data related to authorized users. The machine operates in response to the comparison determining that the bearer card corresponds to an authorized system user to carry out at least one transaction which is operative to transfer value to or from at least one account. A record of the transaction is also commonly printed through operation of the automated banking machine and provided to the user. A common type of automated banking machine used by consumers is an automated teller machine which enables consumers to carry out banking transactions. Banking transactions carried out may include the dispensing of cash, the making of deposits, the transfer of funds between accounts, and account balance inquiries. The types of transactions a customer may carry out with an automated banking machine are determined by the capabilities of the particular machine and the programming associated with operating the machine.

Other types of automated banking machines may be operated by merchants to carry out commercial transactions. These transactions may include, for example, the acceptance of deposit bags, the receipt of checks or other financial instruments, the dispensing of rolled coin or other transactions that are required by merchants. Still other types of automated banking machines may be used by service providers in a transaction environment such as at a bank to carry out financial transactions. Such transactions may include, for example, the counting and storage of currency notes or other financial instrument sheets, the dispensing of notes or other sheets, the imaging of checks or other financial instruments and other types of service provider transactions. For purposes of this disclosure, an automated banking machine, an automated transaction machine or an ATM shall be deemed to include any machine that may be used to electronically carry out transactions involving automated transfers of value.

Automated banking machines may benefit from improvements.

SUMMARY OF DISCLOSURE

An automated banking machine that operates responsive at least in part to data read from data bearing records operates to cause financial transfers to or from financial accounts of machine users. The exemplary machine and system provides enhanced security to assure that risks of fraudulent transactions are reduced. Other exemplary arrangements provide for improved user interfaces for operation of automated banking machines. These include improved user interfaces for persons to operate the machine utilizing wearable mobile devices. Other example arrangements provide user interfaces that enable users that are blind or have impaired vision to operate the machine more conveniently and readily.

Other exemplary arrangements provide capabilities for enabling users to achieve a more sanitary operating environment in connection with items that are provided by the machine. Other example arrangements provide for the capability of dispensing articles which are produced and/or configured through operation of the machine, to include data representative of value and which can be used or redeemed for goods or services.

Further exemplary embodiments will be made apparent in the following description of exemplary embodiments and the appended claims.

BRIEF DESCRIPTION OF DRAWINGS

FIGS. 13-17 are a schematic representation of steps carried out by an exemplary controller of an automated banking machine in connection with dispensing disinfected items.

FIG. 18 is a schematic view of software architecture used in connection with an exemplary arrangement of an automated banking machine.

DETAILED DESCRIPTION OF EXEMPLARY EMBODIMENTS

Figure 1:
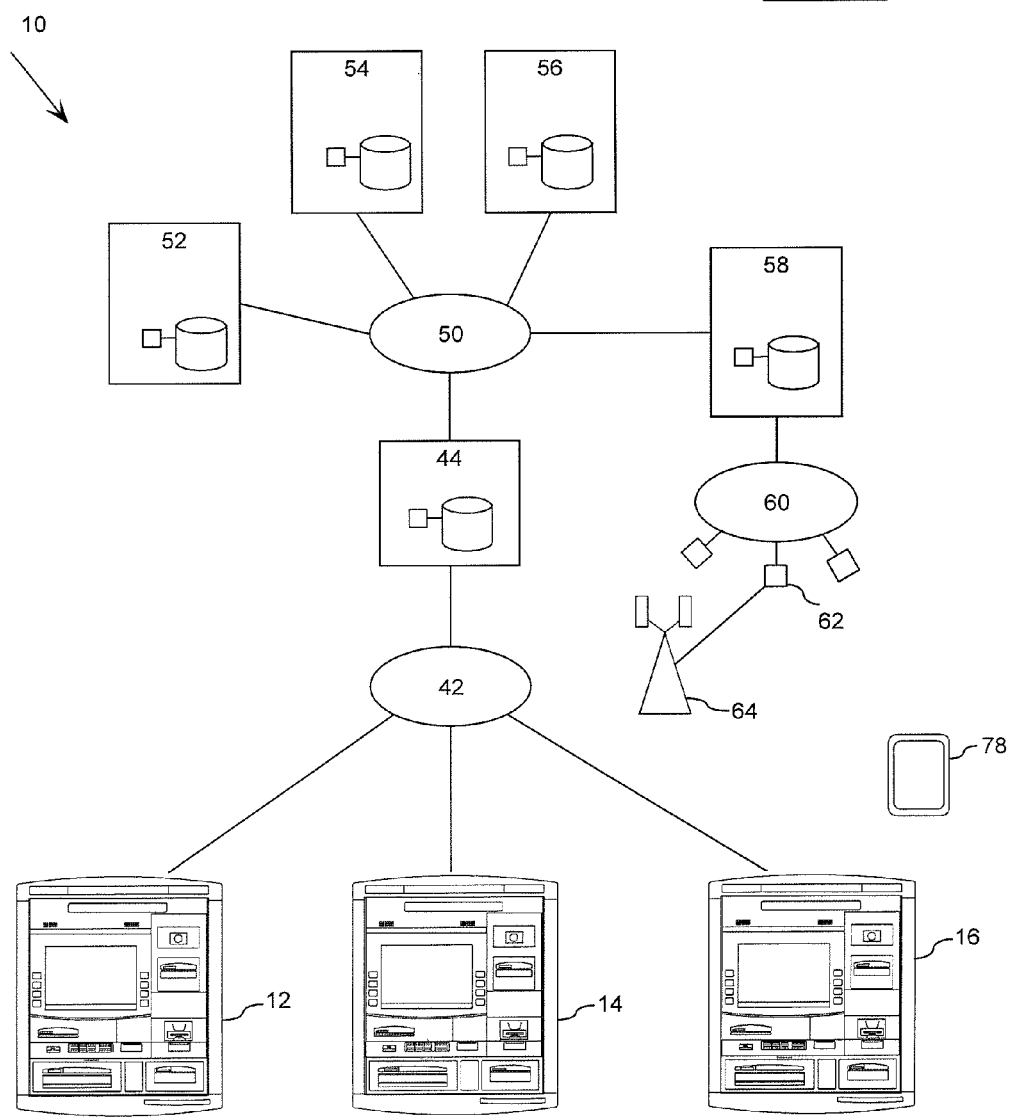
FIG. 1 is a schematic view of a system of an exemplary arrangement including automated banking machines that are operated in response to data read from data bearing records.

Referring now to the drawings and particularly to FIG. 1, there is shown therein an exemplary system 10. System 10 includes a plurality of automated banking machines 12, 14 and 16. Each of the automated banking machines of the exemplary system is operative to cause financial transfers at least one of to or from user financial accounts responsive at least in part to data read from data bearing records. It should be understood that these automated banking machines are exemplary and in other arrangements other types of automated banking machines may be used.

Figure 2:
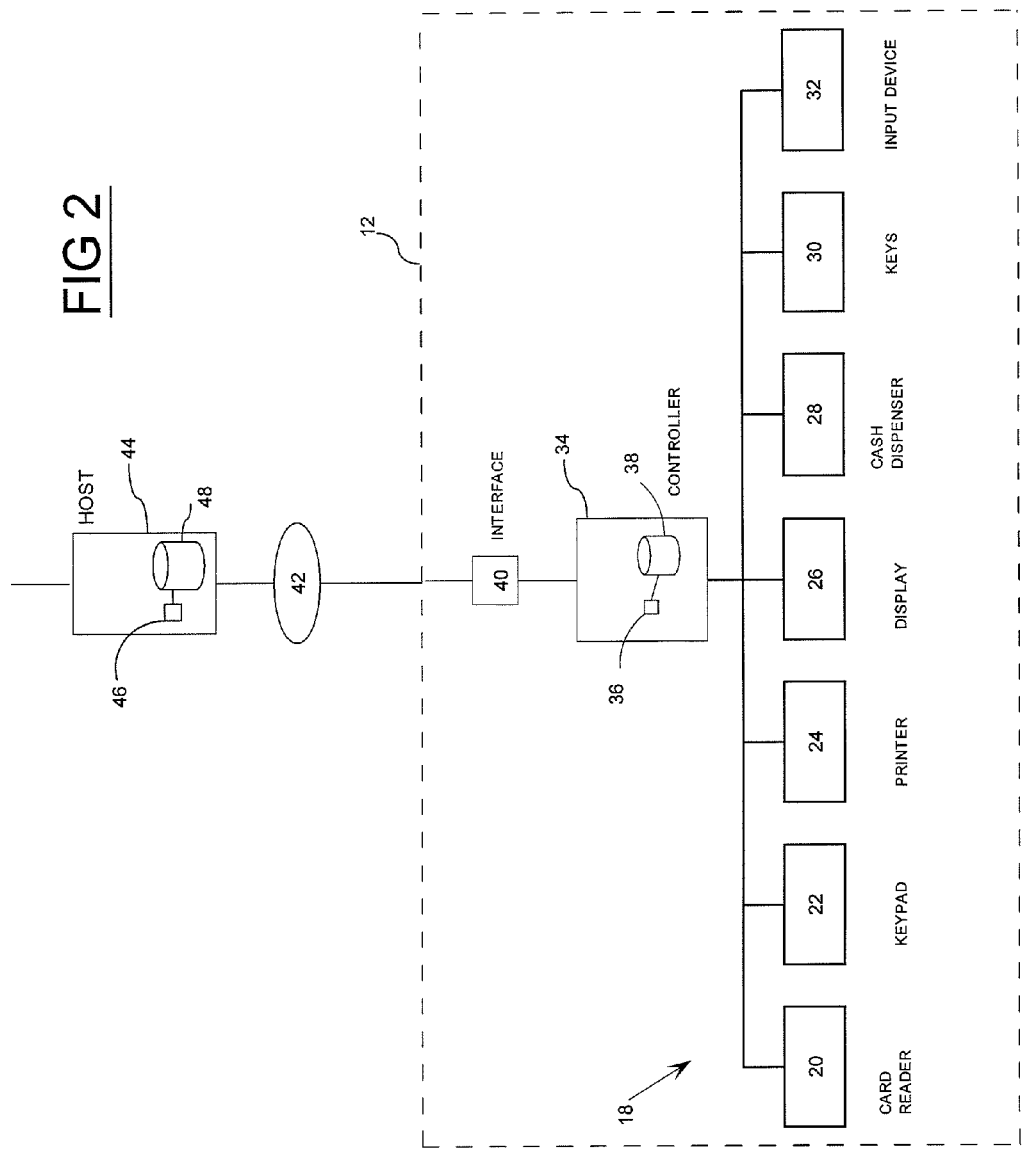
FIG. 2 is a schematic view of the components of an exemplary automated banking machine.

The components of the exemplary automated banking machine 12 are shown schematically in FIG. 2. Automated banking machine 12 includes a plurality of transaction function devices 18. The exemplary transaction function devices in automated banking machine 12 include a card reader 20. Card reader 20 is operative to read data from bearer records such as user cards. The data read through operation of the card reader is usable to identify at least one financial account on which transactions at the machine are to be conducted. The exemplary arrangements may include magnetic stripe card readers, chip type card readers, wireless type card readers or other types of contact or non-contact devices for reading articles which include data that corresponds to financial accounts. In some exemplary arrangements the automated banking machine may include card readers and other features like those described in U.S. Pat. Nos. 7,004,385; 7,284,692; 7,992,776; 7,992,778; and 8,540,142 the disclosures of each of which are incorporated herein by reference in their entirety.

The exemplary automated banking machine further includes a keypad 22. The exemplary machine includes a keypad having a plurality of manually actuatable keys that may be used by machine users to provide inputs. Inputs provided may include alphanumerical inputs or other types of inputs as appropriate to be provided by users for operation of the machine. In exemplary embodiments the keypad may include an encrypting keypad (alternatively referred to herein as an encrypting PIN pad or EPP) which includes internal circuitry that is operative to encrypt inputs that are provided through the keys. Some exemplary arrangements may include features like those shown in U.S. Pat. Nos. 8,540,146; 8,517,262; 7,904,713; 7,896,228; and/or 7,418,592 the disclosures of each of which are incorporated herein by reference in their entirety.

The exemplary automated banking machine 12 further includes a printer 24. Printer 24 of the exemplary arrangement is operative to print paper documents for users of the machine. In some exemplary arrangements the paper documents may include receipts for transactions conducted at the machine. In other exemplary arrangements the printer may be operative to print other documents such as vouchers, scrip, checks, postage or other financial instruments. Some exemplary arrangements may include features like those shown in U.S. Pat. No. 8,424,755 the disclosure of which is incorporated herein by reference in its entirety. Various types of printers may be used in exemplary arrangements such as impact printers, dot matrix printers, laser printers, thermal printers or other suitable types of printers for producing the documents desired to be produced by the machine. It should be understood that some exemplary arrangements may include multiple different types of printers, each of which produce different types of documents that are provided to machine users. Alternative arrangements may include record producing devices that produce records of transactions and store them electronically as an alternative to, or in addition to, on paper or other tangible media.

The exemplary automated banking machine further includes a display 26. Display 26 is operative to provide visual outputs to users of the machine. The visual outputs in the exemplary embodiment include instructions to users concerning the operation of the machine. Displays in some exemplary embodiments may include liquid crystal displays, CRT displays, OLED displays or other types of displays that are suitable for providing visual outputs to users.

The exemplary automated banking machine 12 further includes a cash dispenser 28. In some exemplary arrangements the cash dispenser includes one or more mechanisms that are operative to make cash such as currency bills, coin or other currency items stored within the machine selectively available to users of the machine during the course of transactions. In some exemplary arrangements cash dispensers may include mechanisms that operate to provide currency bills to users. For example in some arrangements the cash dispenser and automated banking machine may include features like those described in U.S. Pat. Nos. 8,128,083; 7,261,236; 7,144,006; 6,981,638; and/or 6,945,526 the disclosures of each of which are incorporated herein by reference in their entirety.

Further in other arrangements the cash dispenser 28 may include a currency recycling device. Such currency recycling devices may include for example devices that enable a machine to receive currency bills from users, to validate the received currency bills as genuine, and store such bills within the machine for later dispense to other authorized users. For example some automated banking machines of exemplary arrangements may include features like those shown in U.S. Pat. Nos. 8,251,281; 8,191,771; 8,132,718; 7,992,775; 7,748,615; 7,891,554; 7,971,781; 7,934,642; 6,682,068; 6,131,809; and/or 6,331,000 the disclosures of each of which are incorporated herein by reference in their entirety.

The exemplary automated banking machine further includes a plurality of manually actuatable function keys 30. In some exemplary embodiments the function keys may be disposed at locations adjacent to the display so as to enable users to manually actuate selected keys to make selections output through the display and to provide inputs to the machine. Alternatively other exemplary embodiments may include other types of keys for receiving inputs from users. Such keys may include other arrangements for manually actuatable keys such as a keyboard or other key arrangement. Further in some exemplary arrangements the display may include a touch screen type input device which may include visual representations of keys which can be selected by authorized users to provide inputs to the machine. Of course these types of keys are exemplary of input devices through which users may provide inputs to the machine.

The exemplary automated banking machine 12 further includes an input device 32. Input device 32 in some embodiments includes a wireless portal that is suitable for receiving and communicating wireless signals. This may include for example communicating signals via radio frequency, infrared, Bluetooth™ or other signals that may be received from or communicated with portable wireless devices such as smart phones, portable tablet devices, wearable computers or other items. Further in other exemplary arrangements other types of communications devices may be utilized for receiving inputs and providing outputs from the machine. Of course it should be understood that these transaction function devices 18 are exemplary and in other arrangements, other or additional devices may be used.

The exemplary automated banking machine 12 includes at least one controller 34. The exemplary controller 34 includes one or more circuits which are operative to communicate electrical signals with and control the operation of transaction function devices 18. In the exemplary arrangement the at least one controller 34 includes at least one processor schematically indicated 36 and at least one data store schematically indicated 38. In exemplary arrangements the processor may include a microprocessor suitable for carrying out computer executable instructions that are stored in the one or more associated data stores. The processor includes or is in connection with a non-volatile storage medium including instructions that include a basic input/output system (BIOS). The exemplary arrangements may include, for example, processors produced by Intel Corporation such as Intel Pentium processors or Intel iCore series processors. Of course it should be understood that these processors are exemplary of many types of processors that may be used.

The exemplary data stores used in connection with exemplary embodiments may include any one or more of several types of mediums suitable for holding computer executable instructions. This may include, for example, magnetic media, optical media, solid state media or other types of media such as RAM, ROM, PROMs, flash memory, computer hard drives or any other form of media suitable for holding data and computer executable instructions. Some exemplary embodiments may include features like those described in U.S. Pat. No. 8,474,698 the disclosure of which is incorporated herein by reference in its entirety. Exemplary controllers may include other components such as hardware and/or software interfaces for communication with the transaction function devices.

The exemplary automated banking machine 12 further includes at least one interface 40. Interface 40 may include, for example, a suitable network interface that enables communication between the at least one controller 34 in the banking machine and one or more networks schematically indicated 42. Interface 40 may include one or more circuits which include electrical components suitable to communicate with wired, optical or wireless networks as appropriate for purposes of providing communications with the machine.

As shown in FIGS. 1 and 2 automated banking machine 12 may communicate through one or more networks 42 with one or more host computers schematically indicated 44. First computer 44 includes at least one processor schematically represented 46 which is in operative connection with at least one data store schematically indicated 48. The processor and data store associated with host computer 44 is operative to carry out computer executable instructions that are stored in at least one data store.

As represented in FIG. 1 in the exemplary arrangement, host computer 44 is in operative communication through one or more networks 50 with financial transaction servers 52, 54 and 56. Each of servers 52, 54 and 56 each include at least one processor and at least one associated data store as schematically shown.

In the exemplary arrangement the system further includes at least one remote computer 58. In the exemplary arrangement at least one remote computer 58 is in operative communication with the system through network 50. Remote computer 58 includes at least one processor and at least one data store as schematically shown. Further in the exemplary arrangement remote computer 58 is also in operative connection with other networks such as network 60 that is schematically shown, as well as other servers 62. Further in the exemplary arrangement the at least one remote computer 58 may be in operative connection with wireless communication networks as schematically indicated 64 as well as other types of public or private networks. The configuration of the particular system will depend on the nature of the system and the types of transactions to be conducted.

In operation of the exemplary arrangement a user at an automated banking machine such as automated banking machine 12 is enabled to carry out transactions involving a user's financial account. This is accomplished in the exemplary arrangement by a user providing to the card reader of the machine, a suitable card such as a credit or debit card that includes card data that is usable to identify the financial account associated with the user. The controller 34 of the exemplary automated banking machine is operative in accordance with its programming to cause the card reader to read the data from the user card. The controller further operates to cause the display to output indicia that prompts a user to input other identifying data to the machine such as a personal identification number (PIN) through the keypad 22 of the machine. The controller then operates to cause the user input PIN or other identifying data to be received through the keypad. Alternatively in some arrangements other or additional identifying data may be received. Such data may include biometric data such as a fingerprint input through an input device such as a fingerprint reader. Other identifying data may include a facial recognition scan, an iris scan, a retina scan, voice recognition or other suitable identifying data that may be input via an input device which can receive such inputs. For purposes hereof each of such types of user identifying input data will be referred to as a PIN.

In the exemplary arrangement the controller 34 operates in accordance with its associated programming to cause the display to output messages to the user which ask the user to select the type of transaction that they wish to conduct through operation of the machine. For purposes of this example, the user will select a cash dispense transaction which the user indicates by providing inputs by pressing the appropriate keys 30 of the machine. In the exemplary arrangement, in response to the user selecting a cash dispense transaction, the at least one controller 34 operates to provide outputs through the display to the user prompting the user to input the amount of cash they wish to have dispensed in connection with the transaction. The controller then operates to cause the user input amount to be received through operation of the keypad 22 or other user input device of the machine.

In response to receiving these items of information from the machine user, the exemplary controller 34 operates in accordance with its programming to cause one or more messages to be sent to the host 44. The messages sent to the host 44 are transmitted through the network interface 40 and through the one or more networks 42 to the host 44. The messages sent by the automated banking machine to the host include data corresponding to the inputs provided by the user to the machine.

In the exemplary arrangement the host 44 operates in accordance with its programming to determine if the data read from the user card corresponds to a user financial account that is authorized to conduct a transaction at the machine. This is accomplished in the exemplary arrangement by the processor 46 of the host 44 determining if the card data corresponds to data stored in the one or more data stores 48 associated with the host. In this exemplary arrangement if the data read from the user card corresponds to an account that is authorized to conduct a transaction through operation of the machine, the host then determines if the customer input PIN corresponds to user identifying data associated with that particular account. This is accomplished by comparing data corresponding to the input PIN to data stored in the at least one data store 48. Thereafter if the PIN data that is input corresponds to the PIN associated with the account, the host computer then operates in accordance with its programming to determine if the financial account of the machine user includes a balance that is at least equal to the amount that the user has requested to be dispensed from the automated banking machine. The host computer does this by comparing the financial account data stored in one or more data stores regarding the balance in the account to the amount requested by the machine user.

If the host computer determines that the card data and PIN data are authorized and that the user's account has sufficient funds to enable the user to withdraw the amount requested, the host then operates in accordance with its programming to send one or more messages to the automated banking machine. The messages sent by the host computer are indicative that the transaction requested by the user is authorized to be carried out. Of course it should be understood that in the event that the card data does not correspond to the account of a user authorized to conduct a transaction at the machine or if the PIN data is not appropriate for that account, then the host computer will send one or more messages to the machine that indicate that the transaction is not authorized. Likewise if the host computer determines that the user does not have a suitable balance in their account to cover the requested cash withdrawal, the host computer will likewise send one or more messages indicating that the transaction is not authorized. In cases where it is indicated that the transaction is not authorized, the at least one controller 34 operates in accordance with its programming to provide one or more outputs through the display 26 to indicate to the user that the transaction is declined. The exemplary controller further operates in accordance with its programming to return the user's card to the user through operation of the card reader. Thereafter the machine returns to the waiting state to conduct another transaction that will start with the input of another card.

In the exemplary arrangement if the one or more messages sent by the host to the automated banking machine indicate that the transaction is authorized, the at least one controller 34 operates in accordance with its programming to cause the cash dispenser to operate. The cash dispenser is operated to make available to the user of the machine, cash corresponding to the amount of cash that the user has requested. The exemplary controller also operates in accordance with its programming to cause the printer 24 of the machine to operate to produce a receipt for the user which indicates the details of the transaction including the value of the cash dispensed.

In the exemplary arrangement the controller 34 also includes one or more records in its data store 38 regarding the carrying out of the transaction and the fact that the cash was dispensed. Further the controller operates in accordance with its programming to send one or more messages to the host computer 44 to indicate that the cash dispense was successfully carried out for the user. In response to the receipt of such messages, the exemplary host operates in accordance with its programming to assess a charge to the user's account corresponding to the value of the cash dispensed.

Of course the process described is utilized for authorizing transactions in situations where host 44 has access to the data necessary to authorize financial transfers for the particular user at the machine. In some exemplary transactions, the host 44 may not have direct access to the data associated with the particular user's account that is sufficient to authorize the user's requested transaction. In such arrangements when the host 44 receives the data related to the requested transaction, the host 44 will operate in accordance with its programming to determine that it does not have the capability to determine whether the transaction requested should be authorized. In such arrangements the host 44 operates in accordance with its programming to route the transaction data in one or more messages to the appropriate network such as network 50 which includes the remote server such as server 52, 54 or 56 that can determine whether the transaction should be authorized.

In the exemplary arrangements the transaction data routed to the appropriate remote server is then analyzed in a manner like that previously described in connection with host 44 to determine if the card data corresponds to an account that is authorized to conduct a transaction through operation of the machine. Further the appropriate remote server operates in accordance with its programming to determine if the customer input PIN corresponds to an authorized user of the account and whether the user account has sufficient funds to cover the requested cash withdrawal. The remote server then operates in accordance with its programming to communicate through the network 50 to the host 44, messages which include information on whether the transaction requested is to be authorized or denied. The host 44 then communicates the appropriate messages to the machine. If the transaction is authorized, the machine communicates that it successfully carried out the transaction to the host 44. The host 44 then communicates this information through the one or more networks 50 to the appropriate remote server. The server then causes the user's account to be assessed an amount corresponding to the value of the cash dispensed.

It should be understood that the approaches described are exemplary. In addition other types of transactions such as deposits, account balance inquiries, check deposit transactions, check cashing transactions, converting electronic value stored on a mobile device to cash or vice versa, cash accepting transactions, or other types of transactions may be conducted in other exemplary embodiments. Further exemplary systems may include features like those described in the following U.S. Patents, the disclosures of which are incorporated herein by reference in their entirety: U.S. Pat. Nos. 8,365,985; 8,376, 219; 7,934,644; 7,857,208; 7,844,512; 7,819,309; 7,689,509; 7,653,601; 7,582,944; 7,533,805; and 6,966,487.

In some exemplary embodiments the at least one remote computer 58 operates to identify situations where fraudulent transactions may be occurring. For example in some situations where card data and PIN data for a financial account has been stolen by criminals, numerous fraudulent cards may be produced by criminals in different parts of the country or in various countries of the world. These criminals may conduct numerous frequent transactions on the account until the account balance is depleted. Often these transactions may be occurring at numerous different automated banking machines or at other types of terminals where value is given, such as at a point of sale or service in diverse locations. The fact that numerous transactions are occurring in rapid succession on a given account may not be realized until after the criminals have successfully depleted a significant portion of the funds in the account for which the card and/or PIN data or other authorized user data that enables carrying out transactions has been stolen.

In the exemplary arrangement at least one remote computer 58 is operated to identify situations where transactions are occurring on a particular account and to provide an alert message in the event a particular account is having an abnormally high number of transactions attempted thereon. By determining that a particular account is experiencing an abnormally high level of activity, the remote computer can provide the alert message so as to enable the entity which holds the account to take appropriate action such as to suspend all further transaction activity. Further in the exemplary arrangement the at least one remote computer does not have the capability to identify the account number or other data for the particular account. Rather the remote computer receives encrypted or other data which is unique to each account but which cannot be utilized to determine the actual account number. Thus the at least one remote computer does not have the associated security risks that would be associated with having such actual account data transmitted thereto over wide area networks, or even public networks, which may be accessed by unauthorized persons.

In the exemplary arrangement the host computer 44 as well as each of the remote servers, for example servers 52, 54 and 56, each have associated programming that operates to produce encrypted data that corresponds to the account number data for each transaction that is requested at an automated banking machine. In exemplary arrangements the encrypted data may correspond to a one-way hash or other algorithmic result that is produced from the account number data either alone or in combination with other data. The algorithmic result that is produced results in encrypted data that in the exemplary embodiment is unique to the particular account number, but that may not be used to resolve the account number except by the particular computer that produced the encrypted data. In some exemplary arrangements the encrypted data may be used directly for purposes of comparison while in other arrangements the encrypted data may need to be mathematically manipulated using other values in order to resolve data that may be compared to other data to identify a common account. Further in the exemplary arrangements the host computer 44 and other servers may operate to provide secure communication through the one or more networks 50 with the at least one remote computer 58. Such secure remote communication may include various approaches such as secure socket layer communications or public key cryptography that ensures that the encrypted data sent from the originating computer is multiply encrypted and can only deliver the encrypted data to the at least one remote computer 58. Of course these approaches are exemplary and in other arrangements other approaches may be used.

Figure 3:
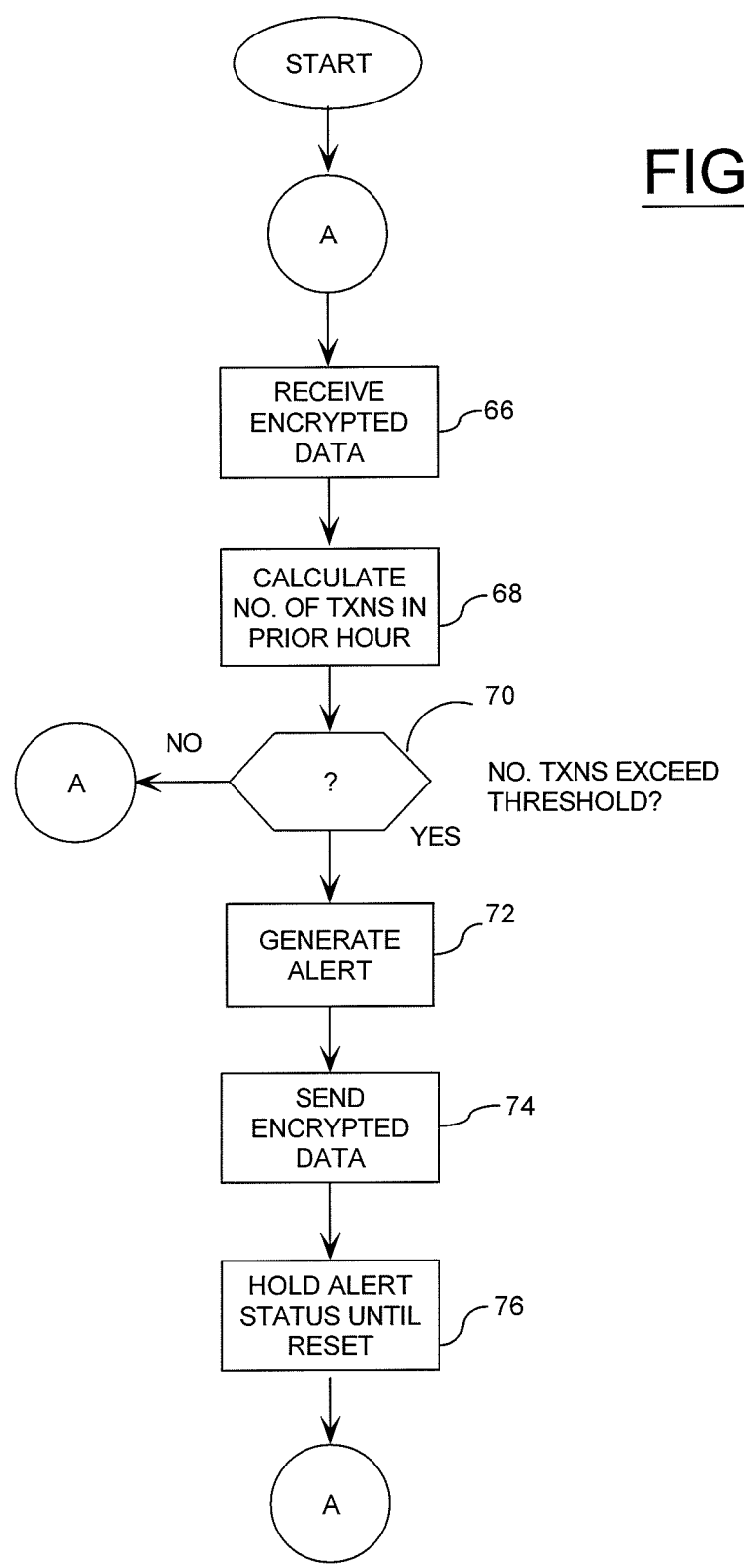
FIG. 3 is a schematic view of steps carried out in operation of at least one remote computer in connection with an exemplary banking machine system.

Logic carried out by the at least one remote computer 58 is represented schematically in FIG. 3. In the exemplary arrangement the at least one remote computer operates to receive the encrypted data from the host computer or server that has received a transaction request related to an account. This is represented by a step 66. The at least one computer then operates in accordance with its programming to review the received encrypted data and to calculate the number of other transactions in which the same or corresponding encrypted data that corresponds to the same account has been received within a prior time period. This may include, for example, a time period which is a rolling window, such as the previous one hour. This is represented by a step 68. Of course it should be understood that this approach is exemplary and in other arrangements other calculations may be made, such as a total number of transactions that have been conducted on the particular account, the elapsed time since the last transaction or the number of transactions that were conducted within a fixed time window. Various approaches may be taken depending on the particular analysis to be conducted to identify an abnormal situation which represents a possible circumstance involving stolen card data.

In the exemplary arrangement the at least one remote computer 58 operates in accordance with its programming to determine based on the calculated number of transactions, whether the transaction count has exceeded a programmed threshold. This is represented in a step 70. If the number of occurrences of receipt of the encrypted data which represents the number of transactions carried out on a particular account, does not exceed the threshold based on the receipt of the most recent occurrence, the computer operates in accordance with its programming to defer any action. However, in the event that the number of transactions has exceeded the programmed threshold within the set rolling time window, the at least one computer operates to generate one or more messages or statuses which comprise an alert. This is represented by a step 72. In some exemplary arrangements the at least one computer may be operated to respond promptly to the received encrypted data so as to indicate to the server or host computer generating the encrypted data that there is a possible problem. This received data in the alert message is usable by the server or host computer to cause a denial of the then pending transaction and/or further transactions which are requested on the account. In alternative arrangements other analysis in accordance with the programming of the remote computer 58 may be conducted. This may include for example evaluating the timing between successive transactions. In this case the computer determines if transactions are happening more quickly than a threshold, and if so, generates a signal corresponding to an alert message. In some embodiments the computer may monitor and evaluate multiple factors in determining whether to generate an alert.

Further in the exemplary arrangement responsive to the generation of the alert, the at least one remote computer 58 is operative to send the data corresponding to the encrypted data to other computers operatively connected in the system that might receive transaction requests related to the account. The sending of this encrypted data to the computers causes the computers to operate in accordance with their programming to store in their associated data stores the encrypted data or other data that is produced when a transaction on that account is requested. Thus by holding the data corresponding to the encrypted data or data that can be used to identify a transaction requested on the same account in the one or more data stores associated with the servers 52, 54 and 56 as well as host 44, such systems may immediately take appropriate steps in accordance with their programming, such as to deny a transaction whenever a transaction on an account is requested and the mathematical manipulation of that account data to produce encrypted data corresponds to the encrypted data for which the alert has been generated. Further in some exemplary systems the receipt of the alert message and encrypted data which can be used to identify transactions which may be suspect, may be utilized by the hosts, servers and remote computer to take steps to try to minimize loss associated with the possible fraudulent transactions. This may include, for example, notifying authorities of the particular transactions which were conducted recently on the account and/or the locations where such transactions occurred. It may also include storing and/or transmitting video surveillance data or taking other appropriate steps that may be useful to identify and apprehend criminals who may be conducting fraudulent transactions on the account.

In the exemplary arrangement the at least one remote computer 58 is operative to maintain the alert status associated with the particular encrypted data until certain programmed steps are taken. For example, such status may be maintained until the at least one remote computer receives messages that the alert status associated with that particular encrypted data should no longer be maintained. This is represented by the step 76.

Of course it should be understood that the foregoing approach to identifying a possible situation where account data has been stolen and is being used fraudulently is exemplary, and in other embodiments other approaches may be used. This may include, for example, including suitable programming in the at least one controller 34 associated with each automated banking machine. Thus for example the controller may be programmed to produce the encrypted data directly and to send this encrypted data either through the associated host or through other connected networks to the at least one remote computer which identifies the possible occurrences of fraudulent transactions on a stolen account. In addition as previously mentioned, in other exemplary systems, rather than having a common approach to producing encrypted data where the same data corresponds to a common account, other approaches may be taken so as to send other data which can be resolved through appropriate programmed steps executed by the at least one remote computer 58 to identify that the encrypted data sent from different sources corresponds to a common account. This may be done, for example, by programming of the automated banking machines, the host computer and the servers in different ways to produce the encrypted data, and by providing programming that enables the at least one remote computer to identify that the different types of encrypted data correspond to one particular account. Further these approaches are useful in the exemplary embodiment because with the remote computer being incapable of determining the actual financial account data from the encrypted data, the financial account data remains secure. This is true even if the encrypted data is transmitted through an insecure network such as the Internet. Of course it should be understood that these approaches are exemplary and in other embodiments, other approaches may be used.

Figure 4:
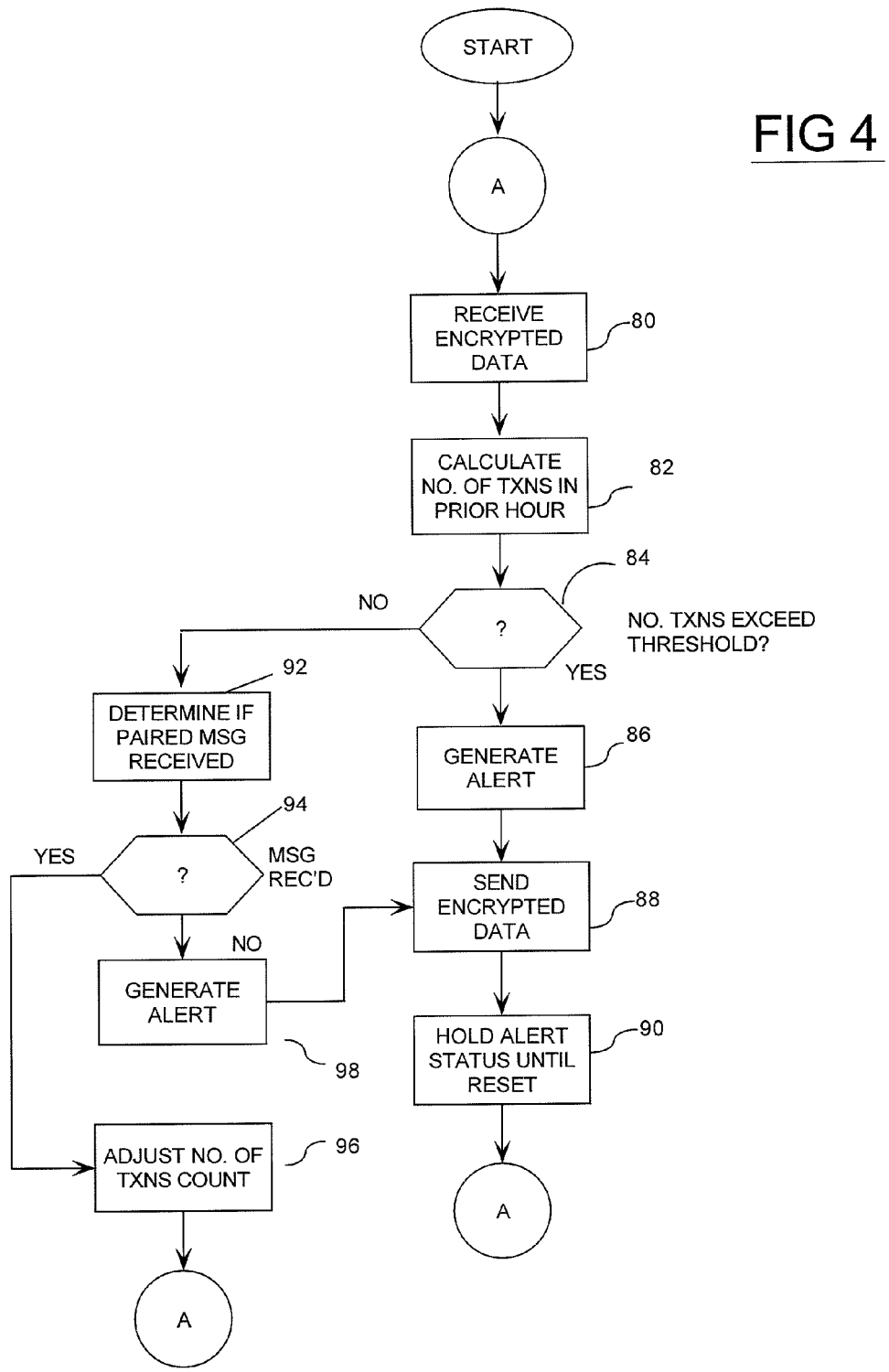
FIG. 4 is an alternative schematic view of steps executed by at least one computer in connection with an automated banking machine system of an exemplary arrangement.

FIG. 4 shows an alternative arrangement in which one or more computers 58 may be operated to identify unauthorized transactions, as well as circumstances where account data may be stolen. In this exemplary arrangement transactions are carried out on the account using a mobile wireless device such as a smart phone 78 represented schematically in FIG. 1. It should be understood that in exemplary arrangements a wireless device may correspond to other types of devices such as tablet computers or wearable computers which are usable by consumers to conduct transactions at an automated banking machine. Alternatively the wireless device may correspond to an article associated with a user such as a user's vehicle which incorporates one or more computers within the circuitry thereof.

In the exemplary arrangement the mobile wireless device is operative to cause data corresponding to the financial account to be sent to the automated banking machine at which the user wishes to conduct a transaction. This may be done, for example, by the mobile wireless device sending data from the device wirelessly through the input device 32 of the automated banking machine. The mobile device may be operative to cause the automated banking machine to receive data that is usable to identify a financial account. This may be done, for example, in some arrangements by the mobile device sending the automated banking machine data which corresponds to an account number directly. Alternatively in some arrangements the mobile wireless device may cause communications with other systems which then cause the automated banking machine to receive data which corresponds to or is usable to resolve the account number. For example in some exemplary arrangements systems may include features like those described in the following U.S. Patents which are incorporated herein by reference in their entirety: U.S. Pat. Nos. 8,281,989; 8,376,221; 8,474,707; 8,052,048; 7,216,800; 7,201,313; and 8,480,307. Of course these approaches are exemplary and in other arrangements other approaches may be used.

In the exemplary arrangement at least one processor included in circuitry of the mobile wireless device 78 may operate in accordance with its programming to cause encrypted data that corresponds to the financial account on which a transaction is to be conducted to be sent to the at least one remote computer. This may be done for example through communication via wireless networks 64. Further as the automated banking machine host computer or server which receives the requested transaction also sends encrypted data that corresponds to the account, this enables the at least one remote computer to identify a common pair of communications having encrypted data that are both received close in time for each authorized transaction. The at least one remote computer 58 is programmed to identify circumstances where both instances of the encrypted data for the given transaction have not been received and to identify such circumstances as a possible situation where a fraudulent transaction may be occurring. The logic associated with such a remote computer that identifies such circumstances is represented in FIG. 4.

In this exemplary arrangement the at least one remote computer 58 receives the encrypted data associated with the account either from the mobile wireless device, server, host or automated banking machine as represented in step 80. As in the prior example the at least one remote computer that operates to calculate the number of transactions indicated as attempted on that account within a given time period. This is represented by a step 82. If the number of transactions is determined to have exceeded the threshold, as represented in a step 84, the at least one computer executes steps similar to those in the prior example. These include generating an alert, sending the encrypted data to the remote systems and holding the alert status until it is reset. This is represented in steps 86, 88 and 90 respectively.

In this exemplary arrangement, in situations where the at least one remote computer is expecting to receive two paired messages in closely spaced time relation in order to indicate that a transaction is authorized, the at least one computer operates in accordance with its programming to determine if the two paired messages associated with the one transaction were received. This is accomplished by the at least one remote computer comparing the messages received with the encrypted data that corresponds to the particular account and the timing associated with the receipt thereof. This is represented in a step 92. A determination is made in a step 94 concerning whether the two paired messages for the common transaction were received. If the two paired messages for the single transaction were received close in time as would be normally expected, then the at least one remote computer 58 operates in accordance with its programming to not indicate that there is a problem. In the exemplary arrangement the at least one remote computer operates in accordance with its programming to adjust the transaction count of transactions on the account to accommodate that two messages are received for each transaction. This is represented in a step 96. Thereafter the at least one remote computer operates to continue to monitor for any potentially problematic conditions.

However, if in the step 94 it is determined that paired messages from the mobile wireless device and from the automated banking machine, host computer or server computer receiving the transaction request were not both received, the computer operates in accordance with its programming to identify an abnormal condition and to generate an alert. This is represented in a step 98. As can be appreciated, the absence of both messages of the expected pair may represent a circumstance where a transaction has been attempted by a criminal or unauthorized person who is not using the authorized mobile wireless device, but is instead providing the account data from an unauthorized source such as a counterfeit card or other fraudulent input device. Alternatively the condition may represent the circumstance where criminals have set up a fraudulent terminal to receive transaction data so as to capture the data for purposes of conducting fraudulent transactions. In either case these circumstances represent a suspect condition.

In the exemplary arrangement the computer operates in accordance with its programming to identify that there is an abnormal condition associated with the account as appropriate to the other computers in the systems. This will enable such computers to identify further attempted transactions on the account and to deny them in accordance with their programming. Further the at least one computer operates in accordance with its programming to hold the alert status associated with the account until it is reset.

Of course it should be understood that these approaches are exemplary and in other embodiments, other additional steps and arrangements may be taken similar to those described herein for purposes of identifying suspect transactions and for denying such transactions and reporting criminal activity.

Figure 5:
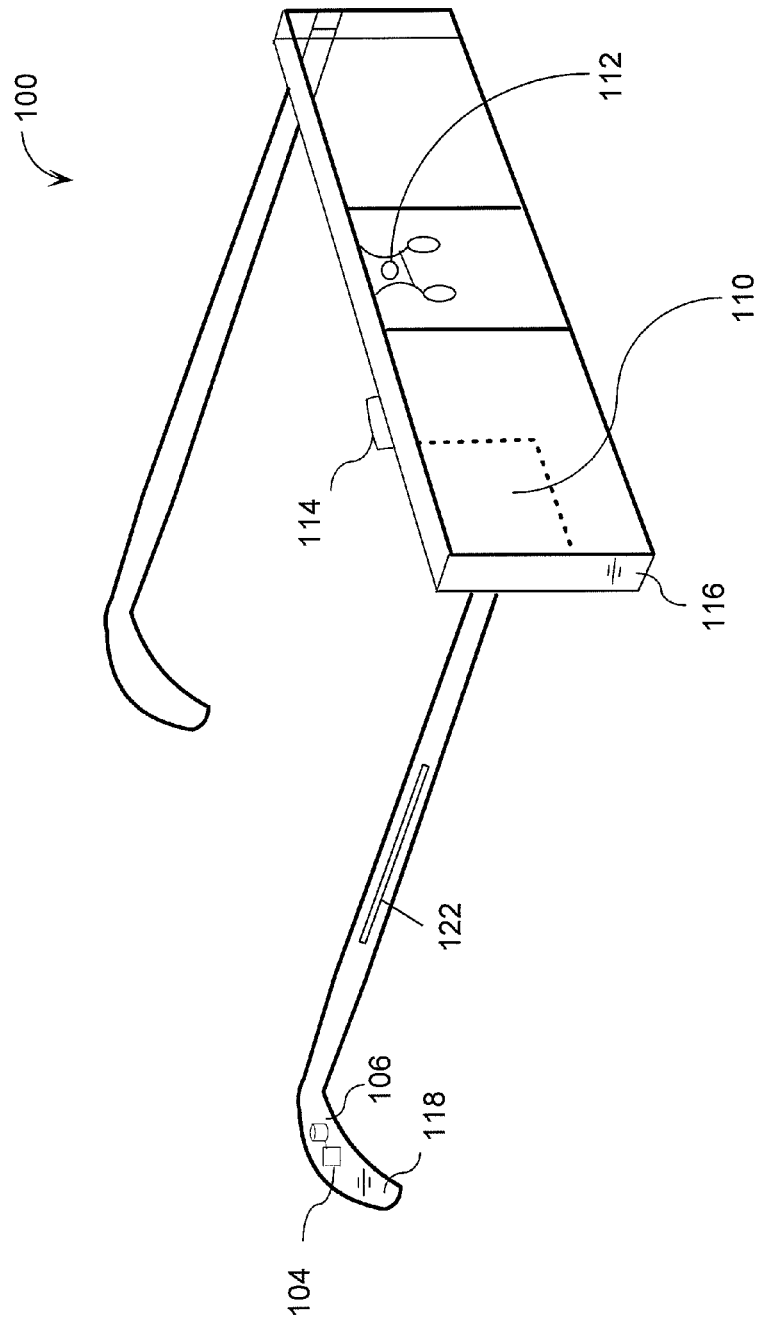
FIG. 5 is an isometric view of an exemplary user wearable mobile wireless device.

FIG. 5 shows an exemplary arrangement of a mobile wireless device generally indicated 100 that may be used in connection with an automated banking machine or otherwise for purposes of carrying out financial transactions. The exemplary device 100 is configured as wearable glasses. However, it should be understood that in other arrangements other configurations of devices may be used. For example, configurations similar to that of a wrist watch, a medallion or a hat or other item of clothing may be used. The exemplary embodiment of device 100 includes at least one circuit which is operative to control the operation of devices that are included as part of the mobile wireless device. The at least one circuit designated 102 in FIG. 6 includes a processor 104 and an associated data store 106.

The exemplary arrangement further includes a source of electrical power such as a battery 108. The exemplary arrangement further includes a generally transparent display 110, an outward facing camera 112 and an inward facing camera 114. The exemplary embodiment further includes a microphone 116 and a speaker 118. The exemplary embodiment further includes a wireless transmitter 120. The wireless transmitter 120 is suitable for transmitting wireless signals between the mobile wireless device 100 and other devices. The wireless transmitter 120 may include a short range wireless transmitter such as a short range RF transceiver or a Bluetooth™ transceiver. Alternatively the wireless transmitter may include an infrared transceiver. Alternatively the wireless transmitter may include a transceiver suitable for communication via a cellular telephone network or other wireless network. Further in some arrangements of the mobile wireless device the apparatus may include multiple types of wireless transceivers depending on the nature of the communications to be carried out through operation of the device.

Figure 6:
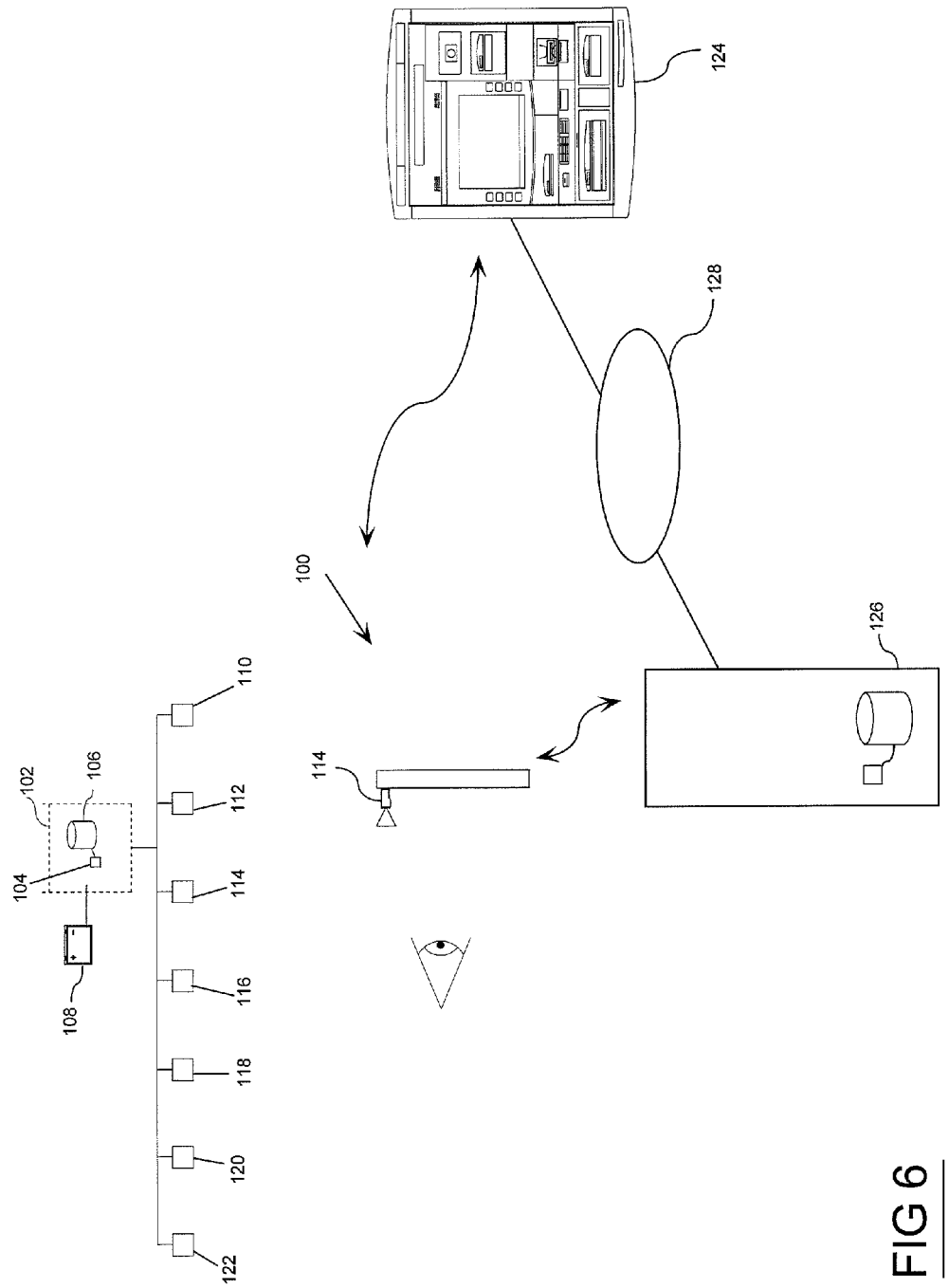
FIG. 6 is a schematic view showing components of the wearable mobile wireless device operating in connection with components of an automated banking machine system.

As represented in FIG. 6, exemplary embodiments of the mobile wireless device may operate to carry out financial transfers. This may be done through communication with an automated banking machine in one of the ways described in the incorporated disclosures. In other arrangements the mobile wireless device may cause financial transfers through communications via a cellular network, a local wireless network or other local or wide area network. The exemplary mobile wireless device is operative to include data in its data store that is usable to identify a financial account. In the exemplary arrangement the data store of the mobile wireless device also includes data that corresponds to a user biometric feature. In some exemplary arrangements this may include programming in the data store that includes data that corresponds to the topography of an authorized user's iris topography of one or both of the user's eyes. The user's iris topography uniquely identifies the authorized user and can be captured through the use of at least one inward facing camera 114. Further in some exemplary arrangements the mobile device may include multiple inward facing cameras or other cameras that can capture iris topography of both irises of the authorized user. In addition or in the alternative other mobile devices may include capabilities for identifying a user's facial topography, retina features and/or other biometric features that can be utilized to identify the user.

Responsive to the inward facing camera or cameras 114 capturing data corresponding to the user's iris topography or other identifying data, the circuitry 102 may operate in accordance with its programming to verify that the mobile device is being operated by the authorized user. This may be done by comparing captured electronic image data to stored data to determine whether there is correspondence or another predetermined relationship which indicates the user is an authorized user. Responsive to such verification determination the authorized user may then provide instructions to the mobile device in connection with carrying out a financial transaction and the mobile device will operate in accordance with its programming to execute instructions responsive to such commands. This may be accomplished in some exemplary arrangements by the user providing spoken commands that are received by the microphone 116 and determined as transaction related inputs through operation of the control circuit 102. Alternatively the user may be presented with menu options or similar options through the display 110, which options the user may select. Selections may be made and input in some embodiments by providing spoken commands that correspond to the options. Alternatively the user may provide selected inputs which enable selecting transaction options output on the display through moving a finger along a tactile sensing bar or other similar input device 122. In still other exemplary arrangements the user may provide inputs through eye movements or line of sight determinations which are detected by the one or more inward facing cameras 114. This may be done for example by utilizing features such as those described in U.S. Pat. Nos. 8,220,706 and/or 7,883,008 the disclosures of which are incorporated herein by reference in their entirety. For example in some exemplary arrangements the circuitry connected with the at least one camera 114 may determine a location where a user eye is looking on the display 10. By determining what particular transaction selections or options the user is looking at, the control circuitry may determine user provided inputs. For example in some instances the user may look at a particular selection being provided on the display and designate that selection by blinking one eye or both eyes. In other arrangements a user may make a selection by speaking a particular word or by providing another perceivable input. When this is done the control circuitry may then operate to provide additional outputs and/or messages that enable carrying out the transaction selected by the user.

As represented in FIG. 6, the mobile wireless device 100 may be used for example to send data associated with a user desired transaction to an automated banking machine 124. Such data may include data such as card data that is usable to identify a user's account. Such data may be stored in the at least one data store 106 and then transmitted wirelessly to the ATM. Further in some arrangements the user may select through the mobile wireless device an account, a transaction type and/or an amount associated with a transaction that they wish to conduct. Data corresponding to these items of information may be included in messages transmitted to the automated banking machine and received through a wireless portal on the machine. This may be done in any one of several ways that are described in the incorporated disclosures or in another suitable manner.

Alternatively in some arrangements the mobile wireless device 100 may communicate data to a server 126 that is remote from the automated banking machine. The server 126 may utilize the data sent from the mobile wireless device to resolve transaction data that is needed by the automated banking machine to carry out the transaction. This may include, for example, account data or other data such as amount data, PIN data or other data that is needed by the machine 124 for purposes of carrying out the transaction. This data may be transmitted from the server 126 to the machine through one or more networks 128. This approach may be utilized, for example, when the mobile device does not include data that directly corresponds to the account information, but rather pseudo data that may be utilized by one or more remote servers to determine the actual account information. Thus for example server 126 may include in its associated data store, data that associates the pseudo data that is provided from the mobile wireless device with the actual account data. The actual account data may then be sent in an encrypted and secure manner to the automated banking machine. This approach may avoid the need, for example, for the mobile wireless device to have included in its data store actual account number data.

Also in other alternative arrangements the mobile wireless device may use its outward facing camera 112 to capture data that is output on the display or other output device of the automated banking machine. Such output data may be used in the manner of the incorporated disclosures to identify a particular machine at which a transaction is to be conducted. This identifying data or data based thereon may then be transmitted to the remote server so as to enable user operation of the automated banking machine. Alternatively or in addition data captured through the outward facing camera of the mobile device may correspond to values, functions and/or instructions that may be utilized for purposes of encrypting account data that is stored in a data store of the mobile wireless device. For example, bar codes such as QR codes output through a banking machine display may provide values or instructions utilized for purposes of encryption of account data. Such encrypted account data may then be sent to either the automated banking machine and/or the remote server for purposes of securing the account data to reduce the risk that it can be intercepted during the transaction. This may be done a number of different ways including those described in the incorporated disclosures as well as in other suitable ways depending on the particular operation of the system.

In this manner a user may accomplish transaction steps through the wearable mobile wireless device or other user device for purposes of carrying out financial transfers. Further it should be understood that although in the exemplary arrangement the mobile wireless device is used in connection with an automated banking machine to accomplish transactions, in other arrangements other devices and systems may be utilized and messages from the mobile wireless device may accomplish financial transfers, account balance checking, bill payment, check capture or other desired transaction operations. For example in some exemplary embodiments the mobile wireless device may utilize an outward facing camera for purposes of capturing an image of a check. The user may provide instructions either verbally or through input devices to capture the image of the check and then cause the check to be deposited in the user's account. This may be done, for example, in the manner shown in U.S. Pat. Nos. 8,418,916; 8,286,867; and/or 8,104,676 the disclosures of each of which are incorporated herein by reference in their entirety.

Further in other exemplary embodiments data corresponding to electronic tickets or other items representative of value may be loaded into the memory of the mobile device. This may be done, for example, through capturing images thereof through the outward facing camera or otherwise through transmission wirelessly to the device. The mobile wireless device may thereafter be utilized to transmit data which may be utilized for purposes of redeeming or utilizing the items of value. This may be done, for example, through approaches described in U.S. Pat. No. 8,387,864 the disclosure of which is incorporated herein by reference in its entirety. Of course these approaches are exemplary, and in other embodiments other approaches may be used.

Further other exemplary arrangements of the mobile wireless device may be useful to accomplish other transaction functions. For example in some exemplary arrangements the circuitry associated with the mobile device may be programmed to identify genuine items of value such as currency bills. This may include, for example, executable program steps that are usable to verify that visible and/or other sensor perceivable authentication features are present in a particular currency bill. Thus, for example, a user may operate the mobile wireless device to capture one or more images of a currency bill through operation of the outward facing camera 112. This may be done, for example, by the programmed instructions associated with the mobile device instructing a user through audible prompts or the visual outputs through display 110 to look at certain features on a currency bill. The control circuitry of the mobile wireless device may operate to utilize the eye tracking capability to monitor the eye or eyes of a user to direct or analyze areas in the field of view the outward facing camera at which the user is looking to a series of features that may identify a currency bill as genuine. In this way the front and/or back of a currency bill may be analyzed to verify that indicia or other visible features indicative of genuineness of the bill are present. In addition alternative exemplary arrangements may include infrared, ultraviolet and/or spaced cameras for purposes of capturing images of authenticity features. Alternatively a user may be prompted to take certain steps with one or more separate devices. This can include illuminating certain areas with radiation at certain frequencies, testing for magnetic or other sensed properties. The camera may capture features or indications of properties or characteristics that are indicative of whether notes are genuine. This approach may be utilized in some exemplary arrangements to enable a user to identify counterfeit or suspect notes that a user receives in a transaction environment and to decline such notes as may appear to be suspect. Further in some example arrangements the wireless communication capability of the mobile wireless device may enable the user to operate the mobile device to analyze, verify or record data in one or more data stores that correspond to the genuine or suspect status of currency bills that are analyzed through operation of the mobile device. Thus in this manner the user can avoid accepting counterfeit currency bills that may be attempted to be passed to the user.

Alternatively or in addition the mobile wireless device may be operative to verify the authenticity of other items or documents. This may include, for example, the capability to identify the genuineness of a credit or debit card through analysis of the visual or other non-contact sensor detectable features included thereon. Thus for example a merchant who wishes to accept a credit or debit card may utilize the mobile wireless device to analyze the features that are on the card including holograms, security codes, or other features that identify the card as genuine. Further in some arrangements such cards or other items may include wireless transmitters or other similar items, such as RFID tags that can be utilized to output signals which can indicate that the card or other item is genuine. The mobile device may include appropriate sensors to capture and analyze such signals and properties and may operate one or circuits that include processors to determine of the card or other item is genuine.

Further in some exemplary embodiments the mobile wireless device can capture image data from the card or other record including for example account number data, verification codes, name data or other items that are usable to carry out a financial transaction. In such arrangements, for example, an operator of the mobile wireless device may utilize the mobile wireless device to obtain the data from a card that is necessary to identify the particular account with which the card is associated and also to verify the genuineness of the card. In this manner by providing instructions to the mobile wireless device, the operator of the device is enabled to accept payments or otherwise accomplish functions that involve a transfer to or from the account associated with the particular card. Such an approach may enable the operator of the mobile wireless device to accomplish the acceptance of credit card and/or debit card payments without a need to have a separate terminal that operates to receive the card, read data from a stripe or computer chip on the card, or otherwise to identify the particular card as genuine and authorized to conduct the transaction.

In still other exemplary arrangements, the mobile device may be utilized to identify features which are indicative of authenticity on articles such as event tickets, gaming tickets, lottery tickets, coupons, vouchers, scrip or other items. In this manner the mobile wireless device may be programmed to utilize image data and/or other data which can be visually or wirelessly read by the device, or with the aid of another device, to determine the genuineness of such articles. Of course these approaches are exemplary and in other embodiments other approaches may be used.

In still other arrangements the mobile device may be utilized to provide useful features in connection with conducting transactions in transaction environments where cash or other items of value are accepted by merchants or similar entities. For example in some establishments, merchants may prefer to receive cash payments for the goods and services they provide. Cash payments have the advantages that they avoid the risks and costs that may be associated with taking payments by either credit or debit cards. Some establishments even provide automated banking machines that dispense cash within their establishment so that users can readily obtain cash for purposes of making purchases. However, such automated banking machines that dispense cash in merchant establishments may commonly charge a fee for purposes of conducting the transaction. This fee may be several dollars in some cases.

In order to facilitate the use of cash in some transaction environments, the establishment may be able to track the serial numbers of currency bills that are dispensed from an automated banking machine to patrons within the establishment. This may be done using features like those described in U.S. Pat. No. 8,474,708, the disclosure of which is incorporated herein by reference in its entirety. In such arrangements the serial numbers associated with dispensed bills may be stored in a data store associated with one or more computer devices that are accessible by the wearable computer devices worn by employees within the establishment. Such mobile wearable computer devices may utilize features like those previously described to evaluate currency bills for genuineness and to also determine the serial numbers thereon. The wearable computer device may communicate the serial numbers from received bills to determine if the bills received correspond to those dispensed by the automated banking machine in the establishment. This may be done, for example, through the use of cameras on a mobile wireless device capturing the serial number data and resolving the data in a manner that can be transmitted wirelessly to the computer which can access the serial number data corresponding to bills dispensed from the banking machine. In cases where a serial number received by an employee is one that was dispensed from the machine, the merchant may offer a credit or a discount to the purchaser. In this way the purchaser is compensated for spending the money that they obtained through use of the machine and paying the surcharge to obtain the cash. Such an approach may be very useful in providing an incentive for individuals to spend the cash that they obtain from the banking machine in the establishment where the machine is located. In addition it may enable the proprietor to evaluate the value of having the machine in terms of how much of the cash that is dispensed therefrom is actually spent by patrons within their establishment. This may be done through programmed instructions associated with one or more computers that evaluate the amounts corresponding to purchases by patrons in the establishment that are based on bills that were dispensed from the machine. Further in the exemplary arrangement the computer data concerning serial numbers of bills that are dispensed from the machine are only held for a limited set period of time. This may correspond in some cases to a one day period, as it would be expected that patrons would likely spend the cash that they receive from the automated banking machine during the same visit to the establishment in which the cash was received. Of course in some establishments the set period may be longer or shorter. After the set period of time, the data concerning the serial numbers of bills dispensed would no longer stored. This avoids the need for creating a large database to hold serial number data associated with dispensed bills. Of course these approaches are exemplary and in other arrangements other approaches may be used.

In some exemplary transaction environments, employees of a particular merchant may have the wearable computer devices provided by the establishment. It may be a requirement of the employment that the employee utilize the wearable computer for business activities during their work hours. In this way, the available functions of the devices can be available at all times when the employee is on duty. In addition in some arrangements the employer may require that each employee store their wearable mobile wireless device in a particular location when it is not in use, such as during off hours when the establishment is closed. In some exemplary arrangements a mounting shelf or stand may be provided onto which the employee may place the wearable wireless mobile device when the employee's shift has ended. The placement of the mobile devices when they are not in use may provide for additional uses of the devices during off hours.

As can be appreciated, the cameras which are utilized on the wearable mobile wireless devices may serve as surveillance cameras during times that the establishment is not open. Such surveillance cameras may be monitored from local or remote monitoring stations so that any intrusions or abnormal conditions can be detected within the establishment. Similarly audio receiving devices included on the wearable computer may be monitored during off hours for purposes of determining abnormal noises which may be indicative of a break-in, machinery malfunction or other problem within the establishment. By having numerous mobile devices positioned in various areas of the establishment during off hours, it may be possible for a monitoring system to observe more areas from more different perspectives than would be possible with stationary security cameras. In addition other detection features of mobile devices such as audible sounds or infrared signals or other things that the wearable mobile devices are capable of sensing, may be utilized in monitoring activities so that such properties may be detected to uncover abnormal or problematic conditions. Of course the capabilities of the wearable mobile wireless devices will determine the capabilities that can be achieved through such arrangements and numerous variations to achieve effective monitoring may be utilized in various arrangements. In some arrangements features similar to those described in U.S. Pat. No. 8,302,856 which is incorporated herein by reference in its entirety, may be utilized.

Figure 7:
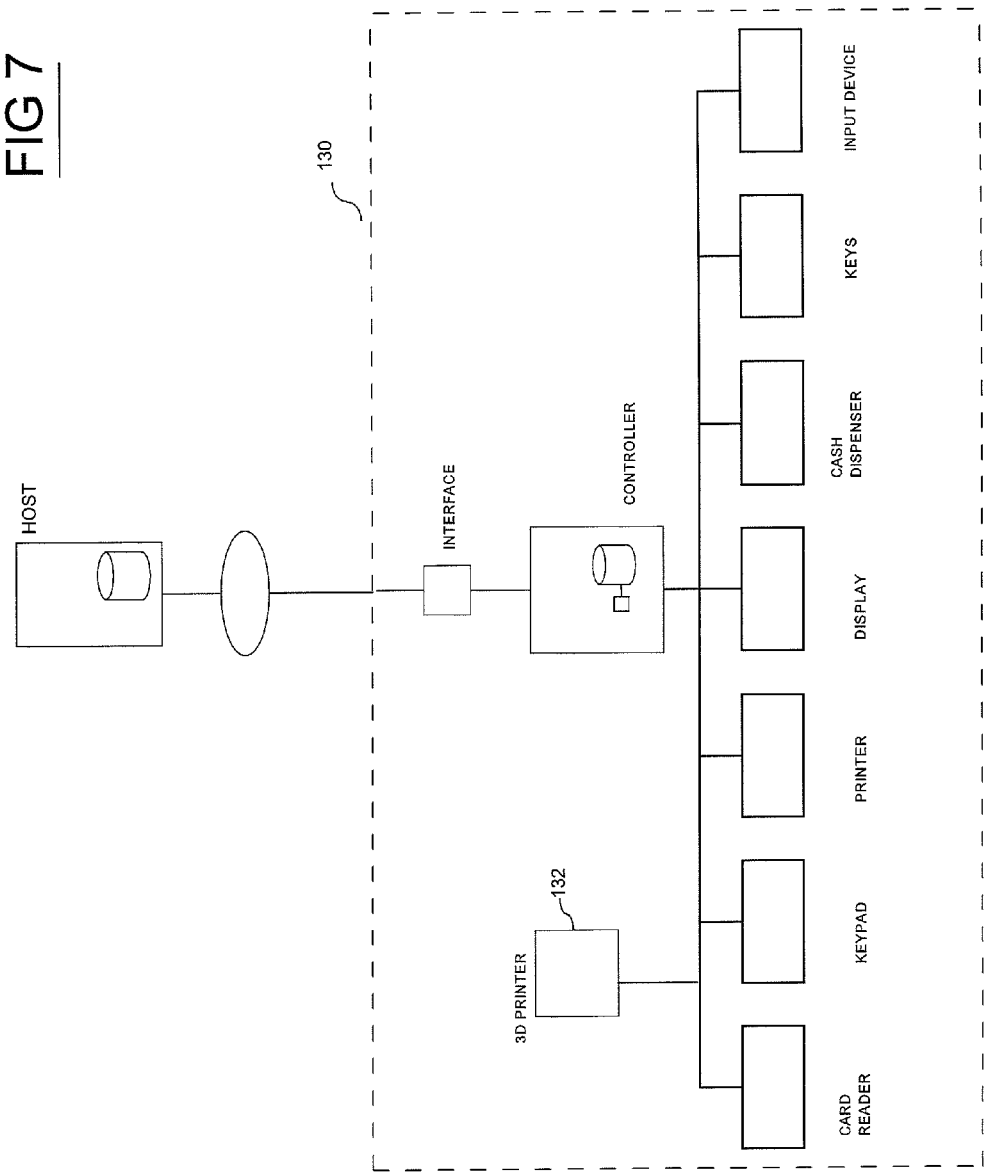
FIG. 7 is a schematic view of components of an alternative exemplary automated banking machine that has the capability of producing or configuring an article for a user.

FIG. 7 shows another exemplary automated banking machine with an alternative arrangement generally indicated 130. Automated banking machine 130 may generally operate in a manner similar to automated banking machine 12 previously described and may include similar components. This alternative embodiment also includes an item producing device generally indicated 132. In the exemplary arrangement the item producing device 132 includes a 3D printer. The 3D printer is utilized to produce items that are dispensed from or otherwise made available by the automated banking machine to a user.

In an exemplary arrangement a 3D printer or other type of material printer is utilized to produce an item that is representative of and is redeemable for value. Specifically in some exemplary arrangements the printer is operative to print patterns of conductive material that comprise RFID tags on a substrate to produce a token. The RFID tags are usable to produce signals corresponding to values that identify the token as genuine and that are associated with or representative of the value for which the token is redeemable.

For example in some exemplary embodiments a user may operate the automated banking machine in a manner similar to that previously described in connection with a cash dispensing transaction. However, in an exemplary alternative arrangement the user may elect through inputs to the machine, to receive a token corresponding to a selected value rather than cash. This would be done, for example, where a user wishes to receive a token that is redeemable for a particular type of merchandise or services available from a particular identified retailer. For example in some arrangements the retailer may offer an additional bonus in terms of goods or services value above the amount that the user pays for the particular token in order to provide an incentive for the user to acquire the merchant's goods or services. Of course this arrangement is one of many that may be utilized in connection with the described features.

Figure 8:
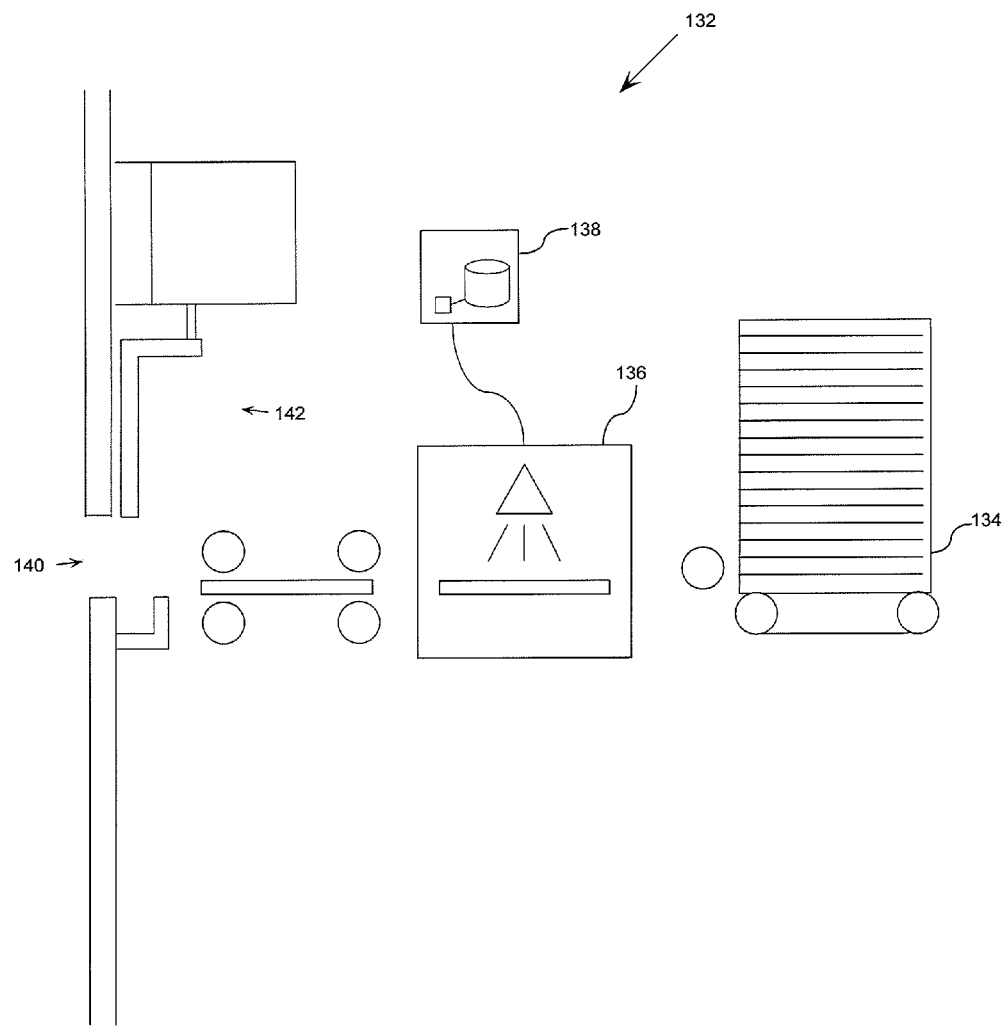
FIG. 8 is a schematic view of a 3D printer operated in connection with articles dispensed from an exemplary automated banking machine.
Figure 9:
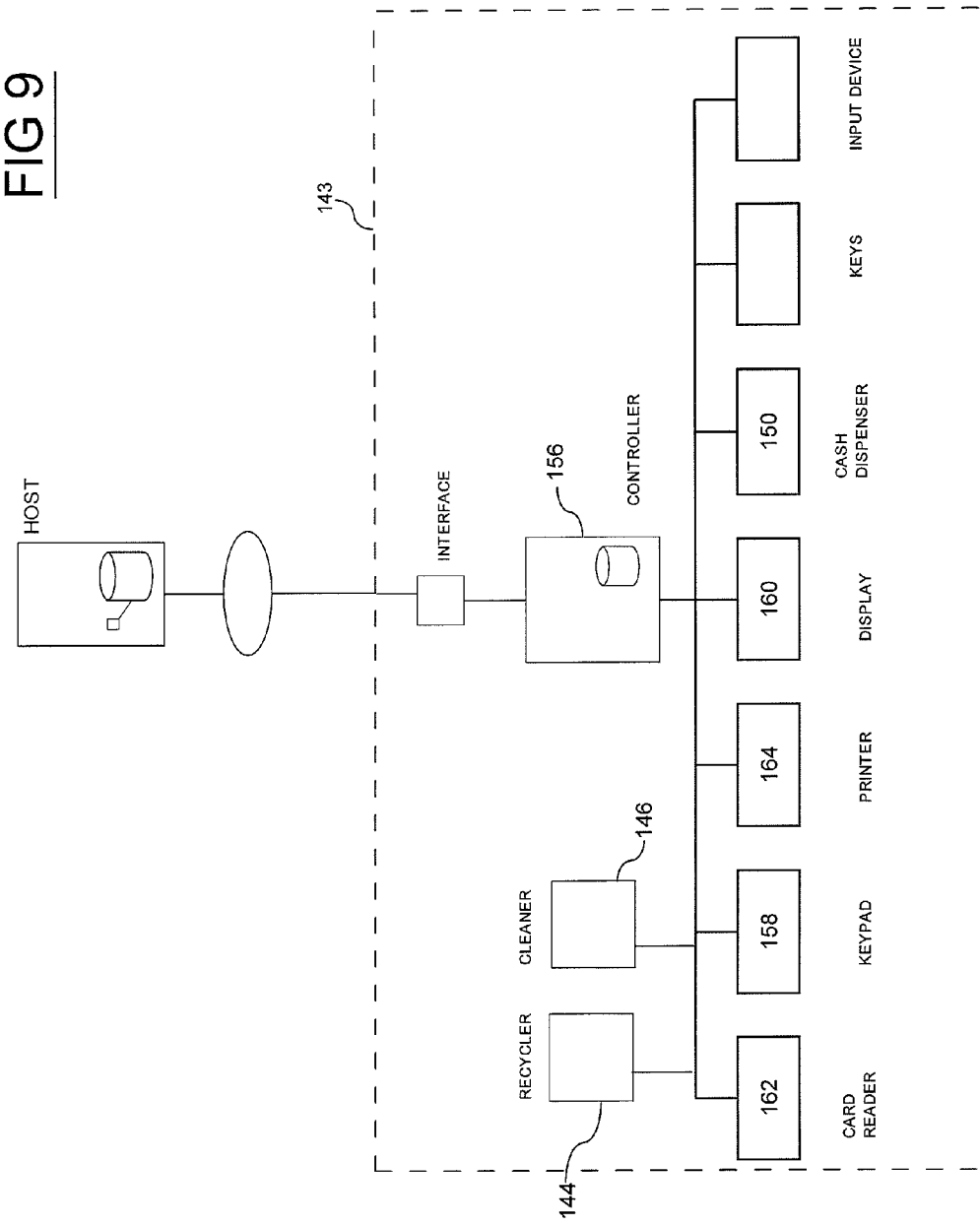
FIG. 9 is a schematic view of an alternative arrangement of an automated banking machine that provides the capability for disinfecting items dispensed from the machine.

In such arrangement the printer may operate as represented in FIG. 8 to produce a token that includes indicia that can be securely redeemed for value by the particular merchant. In this arrangement the printer 132 includes a mechanism that operates to receive a piece of token substrate material from a magazine or similar storage area generally indicated 134. The single item of substrate that is removed from the storage area is then printed upon by applying one or more patterns of metallic conductive material thereon in a printing chamber 136. The printing chamber includes a printing head that deposits the metallic material such as silver or copper inks in patterns that correspond to one or more RFID tags. This is accomplished through control provided by circuit 138. Circuit 138 includes one or more processors and one or more data stores with programmed instructions that are usable to determine the value or values corresponding to the desired tags and to produce the patterns corresponding to the RFID tags that are produced on the token.

It should be understood that in the exemplary arrangement one or more RFID tags that are produced on the substrate correspond to values that are known by the controller of the automated banking machine and that are communicated to one or more remote servers. This enables the token that is produced through operation of the printer to be identified as genuine or otherwise acceptable by RFID tag readers or other items positioned at the locations where the token may be redeemed for goods or services of the merchant. Further as can be appreciated, the RFID tags that are included on the token produced may include security features, encryption features, verification features, redemption indicating features or other items and features that are usable to prevent counterfeiting and assure that the token presented is usable and genuine.

Once the exemplary token has been produced by the printer, it is moved through operation of a suitable conveying mechanism through an opening 140 in the automated banking machine so that the token may be received by a user. As can be appreciated, the opening may be controlled by one or more suitable gate mechanisms 142 or other mechanisms to help assure that access to the interior of the machine and the 3D printer from outside the machine is prevented.

Of course it should be understood that production of tokens corresponding to value is merely exemplary of the types of items that may be produced through operation of an automated banking machine including one or more 3D printers or other printer types. For example in some exemplary arrangements the automated banking machine may be usable to produce plastic sheet materials. Such plastic sheet materials may include embedded metallic or non-metallic materials which may be usable to identify the sheets as genuine and also to indicate the value associated therewith. In addition visible and non-visible elements may also be produced within or on the sheets so as to provide a visual appearance that may indicate to a user the nature and/or value of the particular item. Such items may commonly include items such as scrip, coupons, tickets or other items that are representative of or are redeemable for value.

Further in some exemplary arrangements such items may include embedded items that are included during their production in the machine. This may include, for example, batteries, sensors, output devices, input devices or other suitable items that may be either pre-produced and embedded in the appropriate locations within the item when it is produced, or alternatively produced by multiple different types of 3D printers and/or other printers or devices included in the machine. For example and without limitation, some arrangements may include the capability of the automated banking machine to produce a token, card or similar article that in itself can be operated as a transaction terminal that can be operated by a user to carry out certain types of financial transactions. This may be accomplished by producing an item that includes a wireless transceiver, input and output devices, contact or non-contact connectors and other things necessary to accomplish financial transfers through communication. Such a produced item for example may include the capability of transferring funds in an amount up to the associated value that the user selected in connection with the transaction that resulted in production of the item. Of course this approach is exemplary and many different types of items may be produced utilizing the principles discussed herein.

In some exemplary arrangements the automated banking machine may provide tokens, cards or other articles that include circuits including microprocessors and other electronic components. In some exemplary arrangements the microprocessors and other circuitry may include organic microprocessors and other electronic components. Such components may be produced for example in some exemplary arrangements by depositing thin films of alternating layers of organic material (for example, pentacene and insulators) and metallic materials such as conductive inks for interconnections. Such layers may be deposited onto a substrate such as a plastic material to produce microprocessors and other circuit components that can execute instructions and other circuit component functions, and to provide outputs via card contacts, RF transceivers or other devices that are usable in connection with providing transaction data or other information used for purposes of transactions.

In some exemplary arrangements such technology may be utilized for purposes of providing microprocessors on or in transaction cards that can be used to provide verification of the genuineness of the card. This may include, for example, producing microprocessor circuitry from organic material that carries out algorithmic functions that identify the particular card as genuine or that identifies a particular financial account. These algorithmic functions may be those developed by certain industry standard setting organizations such as EMV. Using such approaches data supplied as signals to circuitry on a card produces a result which identifies an account and/or indicates that the card is the genuine card and not a counterfeit. Such techniques are particularly useful in connection with magnetic stripe cards for which providing the separate circuitry including processor capability is usable to generate verification values that provide an indication that the card is not counterfeit. Thus for example in an exemplary arrangement, data from a magnetic stripe on a card may be read by a card reader to provide account number and other data related to an account on which a transaction can be conducted. In addition, certain inputs to the microprocessor circuitry can be used by the circuitry to produce one or more results. Such one or more output results may be communicated and/or compared or otherwise used for purposes of comparison to data that indicates the genuineness of the card. Different types of algorithms may be used for purposes of the programming of the microprocessors so as to utilize different input values or other parameters to produce results which can be verified as appropriate and corresponding to a genuine card. As can be appreciated, various forms of encryption and decryption and other security functions may also be included in such circuitry that includes the microprocessor.

In some exemplary arrangements an automated banking machine may be operated to apply microprocessor including circuits directly to an area of an existing card. Such microprocessor based circuitry may then be utilized thereafter to verify the genuineness of that particular card. In some exemplary arrangements the microprocessor based circuitry may communicate via direct contact with conductive contacts that engage the circuitry on the card that is applied through printing or other techniques. In other arrangements the applied microprocessor circuit on the card may communicate in a wireless manner via radio signals or other signals similar to RFID tags previously discussed.

In some exemplary arrangements the automated banking machine may operate to take an existing card and with the permission of the user, apply the appropriate circuitry thereto to add verification capabilities that are usable in the future to verify that the card is the genuine card. In other arrangements, the automated banking machine may operate to build for the user a new card or other article that includes appropriate circuitry to verify that the card or article is genuine. This may be done in some arrangements, for example, by having a stored group of cards or other items which serve as the substrate or base part for the articles to be produced. The circuits including microprocessors and other components is then applied to the substrate or base part to produce an article that can be used to provide transaction data such as account number, user name and other information, and then also provides outputs that can be used to verify that the item is genuine.

In still other arrangements, 3D printer technology may be utilized to produce an item without the use of a starting substrate or base part. In some exemplary cases the 3D printer may be operated to produce a card shaped article that includes therein circuitry and other components that enable the use of the article as a credit card or a debit card. This may include, for example, circuits including microprocessors or other devices produced via substance deposition techniques in appropriate configurations. Such circuits are operative to store and securely deliver account data, verification data and other data that can be utilized to carry out transactions. For example card-like articles that wirelessly communicate with automated banking machine card readers can provide account data to be used to carry out purchase or banking transactions through connected terminal devices.

In still other exemplary arrangements, articles may be produced that include appropriate circuits that communicate transaction data and/or other data with other devices so that a user can obtain goods or services through use of the particular item. For example in some exemplary arrangements a 3D printer may be utilized to produce a wearable article for a user that provides account data and other transaction data to systems that communicate with the device. This enables a user to make purchases, transfer funds and carry out other functions without need for interaction with dedicated financial transaction terminals. For example in a transaction environment where a user makes purchases, the user may be provided with a wrist band or pendant that the user can wear while in the area where transactions are enabled to be conducted. Articles that a user can purchase are labeled with RFID tags or other indicators of a price associated therewith. By transporting the items from a location where they can be viewed and are positioned for sale within the establishment, to another area of the establishment such as an area adjacent to the exit, wireless transceivers determine the particular articles that the user is carrying and the user's account identifying data by communication with the wearable article worn by the user in the transaction environment. The user's account may then be automatically charged for the items that are taken.

In alternative exemplary arrangements that article may be produced via 3D printing or other techniques previously discussed, and provided to a user in an area where the user may receive and be charged for services. Such areas may include for example, theme parks, movie theaters or other areas where a user is charged based on where they travel within the establishment. The article provided to the user may wirelessly communicate with sensors located in different areas so that the user's account is automatically charged for the attractions that are visited and/or services received by the user. This may involve wirelessly sensing the presence of the article and receiving the account identifying data therefrom as the user travels adjacent to sensors located at the entrance and/or exits of various attractions/services areas. Thus, for example, in an environment where a user is attending a theme park, the user may be charged for visiting certain premium areas of the park when their portable article is sensed within the premium area of the park.

In some exemplary arrangements, the article produced for the user may correspond to the particular transaction environment in which the article is to be used. For example if the article is to be presented in a theme park, the article may be produced as an attractive pendant including a design based on the logos of the theme park or the characters (such as cartoon or other characters) associated with the theme park. Further 3D printing techniques may be used to include in the transaction article that is produced, personalized information such as the user's name or initials or features selected by a user. For example if a theme park is associated with several different cartoon characters, the article produced for the user could be in the shape of the user's chosen character that is selected via inputs to the automated banking machine that operates to produce the item via 3D printing techniques. Of course these approaches are exemplary and in other arrangements, other approaches may be used.

In still other arrangements, the transaction articles produced may be suitable for generally continuous use in multiple different transaction environments. This would enable the user to use the article that is produced in making purchases of goods and/or services in any establishment where the account data and verification data can be read by suitable sensing equipment. Alternatively such articles produced may be programmed so that they are limited and can only be used during a given period of time. For example in the case of a theme park where a user has purchased a one-day pass, and the transaction article produced through operation of the banking machine may be operable to provide transaction data only during that day. In still other arrangements wireless or contact communication with the article may be used to selectively turn the transaction capabilities of the item on and off. Thus for example if the particular article is a token that is usable for making purchases in a particular type of store, wireless communication or other communication with a transceiver may be utilized to turn on the capabilities of the article to provide account or other transaction data when a user enters the store and the capabilities of the article may be turned off automatically when the user exits. This may be done securely so that user transaction data cannot be obtained from the item by unauthorized persons. Alternatively or in addition provision may be made for the transaction capabilities of the article to be selectively turned on and off by a user. This may be done, for example, by inputs to switches, keypads or other input devices that are included in the article. Such input devices may be included through the 3D printing techniques or other printing techniques for including circuitry and other features in articles as previously discussed.

Further some exemplary arrangements may include using an automated banking machine to produce an article that has additional verification features. Such features may include, for example, circuit components and microprocessors that have the capabilities to receive inputs from users. As previously discussed, such articles may include input devices such as user actuatable keypads or similar devices that can receive personal identification numbers or other codes from a user. Thus for example in some exemplary arrangements an article can be produced for a user that includes a small keypad into which a user can provide a selected input that enables the device to output user account data and/or otherwise carry out transactions until the capability is disabled. Such disabling capability may be provided by the user providing an additional input through the keypad or other device. Alternatively in other arrangements the article may be made so that use of the device in connection with conducting a transaction causes the circuitry therein to be operable responsive to the programming of the circuitry, to disable the operation of the device after a single transaction has been conducted. Thereafter the user would have to provide inputs or otherwise enable the article again if the user desired to conduct another transaction. For example in some arrangements if the article has been transaction enabled via inputs from a user, the article may wirelessly communicate via RF to deliver data corresponding to the user's account and data which indicates the genuineness of the article, in response to signals received from a transceiver associated with a particular merchant terminal or a merchant establishment. In situations where the article was not transaction enabled, the article would not provide such communications and no such transactions could be conducted.

In other arrangements other types of input devices may be included in transaction articles that are produced through operation of the automated banking machine. Such input devices may include, for example, sensors that are suitable for reading biometric inputs such as fingerprints. For example layers of suitable materials for sensing the ridges of a user's fingerprints may be utilized to receive the unique data associated with contact with an authorized user's finger. For example in some arrangements if the user's finger is not currently in contact with the sensing area of a given article, the article will not operate to communicate account data with transceivers that are connected to a transaction system. Alternatively in other arrangements, programming associated with the article may be enabled to remain operative to deliver account or other data for a period of time after the sensing area has been in contact with an authorized user's fingerprint. In still other arrangements other types of sensing devices may be utilized for purposes of verifying codes, images, audible words, voice recognition or other things that are uniquely associated with a user for purposes of verifying that the article is in possession of and is being used by an authorized user to conduct transactions. Of course these approaches are exemplary and in other arrangements other approaches may be used.

In still other exemplary embodiments enhanced security for card based transactions may be accomplished by providing a user with a card, token or other device that may be used as an adjunct to their transaction card when carrying out transactions. As previously discussed, enhanced security for card based transactions is achieved by including a circuit including a microprocessor on or in a card, which circuit executes algorithms and produces results which indicate that the card is genuine. Processor chips may be included on magnetic stripe cards for purposes of verifying card genuineness and reducing the risk that the magnetic stripe card has been counterfeited. In such arrangements the fact that the magnetic stripe of the card includes proper data identifying the user and/or their account and the chip on the card, when properly supplied with certain input signals and/or values produces a particular result, shows that the card is genuine. However, providing users with a card with both a magnetic stripe and a chip may be more expensive or have other drawbacks than providing to the user a card with a magnetic stripe alone. This is particularly true if the user has already received a magnetic stripe card that does not include a processor chip.

In exemplary arrangements in order to provide enhanced security, the user is provided with a separate article that can be used in conjunction with the magnetic stripe card. In some exemplary arrangements the user is provided with a card or token that includes a circuit including a processor programmed with suitable program instructions to produce results that can be used to verify authenticity of a card. Such programmed instructions may correspond to the algorithms developed by EMV Co. and which have been adopted by many transaction processors and card issuers. Of course these approaches are exemplary and in other embodiments other types of algorithms for card verification routines may be utilized.

In some exemplary arrangements the circuitry embedded in the validation device may include wireless communication capabilities so as to enable non-contact communication with a transaction terminal such as an automated banking machine. Such communication may include radio frequency communication of messages with a transceiver positioned in the machine. Such a transceiver may include an RF transceiver positioned within the card reading device of the banking machine that reads the magnetic stripe data on a card. Alternatively the transceiver may be located in another location on the automated banking machine. An advantage of positioning the transceiver in the card reader is that it may be used to communicate with circuits including microprocessors that are embedded in cards that include a magnetic stripe, as well as with separate verification articles that are separate from the magnetic stripe card. For example in some arrangements the transceiver may operate to communicate with the verification article which is positioned in close proximity to the card slot of the automated banking machine. In such arrangement while the card bearing the magnetic stripe is received and read by the card reader, the verification article is placed in close proximity to the card reader slot and communicates with the transceiver so as to receive the initiation messages and provide the results in response thereto so as to confirm the genuineness of the associated magnetic stripe card. Further in exemplary arrangements, the verification article is programmably changeable through communication with the transceiver so that in subsequent transactions the verification results data produced through operation of the circuit and microprocessor on the verification article corresponds to different results required to verify the identity of the magnetic stripe card in such subsequent transactions.

In other arrangements the verification article may include other types of devices. For example in some arrangements the verification article may comprise a wearable computer device which is worn by a user. In such arrangements the programming associated with providing the results data to the transaction terminal which confirms the authenticity of the magnetic stripe card, is provided through communication with the RF transceiver and processor circuitry included in the wearable computer article. The processor included in the wearable computer executes the algorithms that provides the results which verify the authenticity of the card. Further one or more data stores associated with the wearable computer article enables the results to be modified and to correspond to what is required to authenticate the card in subsequent transactions. Further in some exemplary arrangements the wearable computer article may include data for multiple magnetic stripe cards so that each may be authenticated through communication with the wearable article. As a result the wearable computer device can serve as the verification article for multiple magnetic stripe cards.

In still other exemplary arrangements a portable communication device such as a smart phone may include programs that cause the at least one processor in the smart phone to execute the verification algorithms that receive inputs and produce results that can be used to authenticate one or more magnetic stripe cards. Such a smart phone may communicate via radio frequency communication with a transceiver in an automated banking machine so as to receive the initiation data and provide the necessary results which help to prove the authenticity of the card. This may be done via communication by a near field communication, Bluetooth or other suitable communication type.

Thus these exemplary arrangements enable a magnetic stripe card that does not include a processor thereon to nonetheless be verified as a genuine card by a user having possession of the verification article which executes the verification algorithms and provides to a transaction terminal the one or more results that indicate that the card is genuine. Such approaches can be used to avoid the need to deploy magnetic stripe cards that have included thereon processors which execute algorithms to verify the genuineness of the card. Of course these approaches are exemplary and in other embodiments other approaches may be used.

In still other exemplary arrangements remote communications may be utilized for purposes of verifying the genuineness of a transaction card such as a magnetic stripe card. In such exemplary arrangements, a portable device such as a smart phone with the ability to communicate over a wide area network may execute the algorithms that produce results which demonstrate the genuineness of a card. These may include, for example, the EMV algorithms or other algorithms that are normally executed on a microprocessor chip that is resident on a card and/or in a transaction terminal or other computer. Rather than providing short distance RF communication as in the previously described embodiment, such a smart phone or other device may provide other wide area network communications such as via cellular phone or wireless Internet connections to the transaction processing host that processes the card data. The communication of the verification data via the wide area network may be encrypted to further assure that such communications are not fraudulent. Further in order to avoid the risk of fraudulent communications, the location of the verification article which comprises a portable wireless device such as the smart phone, can be determined by the one or more computers associated with the system via global positioning system signals to verify that the device is in proximity to the transaction terminal. This may be done using features such as those disclosed in U.S. Pat. Nos. 8,479,983; 8,505,814; 8,540,147 and/or 8,561,889 the disclosures of each of which are incorporated herein by reference in their entirety.

Of course it should be understood that these approaches may be combined or used in conjunction with other approaches that are described in the incorporated disclosures for purposes of verifying that a transaction that a user is requesting at an automated banking machine or other transaction terminal, is authorized by the user. Such approaches may include, for example, approaches where the user is contacted via their smart phone or other mobile wireless device through an automated system, and requested to provide at least one input to verify that the transaction should proceed. In such arrangements the portable wireless device of the user may operate not only to provide a message to the system to indicate that the transaction should proceed, but may also communicate with the system to receive the necessary initiation data and provide the results which demonstrate that the user card being utilized in connection with the transaction, is genuine. Such systems may utilize features such as those described in U.S. Pat. No. 8,353,450 the disclosure of which is incorporated herein by reference in its entirety. Of course these approaches are exemplary and in other arrangements other approaches may be used.

FIGS. 9-17 describe an alternative automated banking machine generally indicated 143. Machine 143 is generally similar to machine 12 previously described except as otherwise indicated.

Machine 143 includes at least one recycler module generally indicated 144. In exemplary embodiments the recycler may be a belt type recycler. Exemplary arrangements may include features like those described in U.S. Pat. Nos. 6,367,692; 6,367,691; and/or 6,264,102 the disclosures of each of which are incorporated herein by reference in their entirety.

The exemplary embodiment further includes one or more cleaner/disinfecting devices generally indicated 146. In exemplary embodiments the cleaner/disinfecting devices may include one or more ultraviolet radiation emitting devices. Such devices may be operative to emit UV-C or other radiation that operates to kill bacteria and viruses on surfaces, including the surfaces of currency bills (which are alternatively referred to herein as notes). In addition or in the alternative the cleaner/disinfecting devices may also include devices that operate to scrub currency notes and to apply vacuum or other forces designed to cleanse the surfaces thereof of impurities and other unwanted substances. In some arrangements the cleaner/disinfecting devices may be usable to kill disease transmitting organisms that may reside on the surfaces of currency bills. Alternatively or in addition in some arrangements such cleaner/disinfecting devices may be usable to remove undesirable substances such as the residue of illegal drugs or contaminants or other impurities that may be present on bills, so that such substances cannot be detected or absorbed through the skin by persons who receive and handle such bills.

Figure 10:
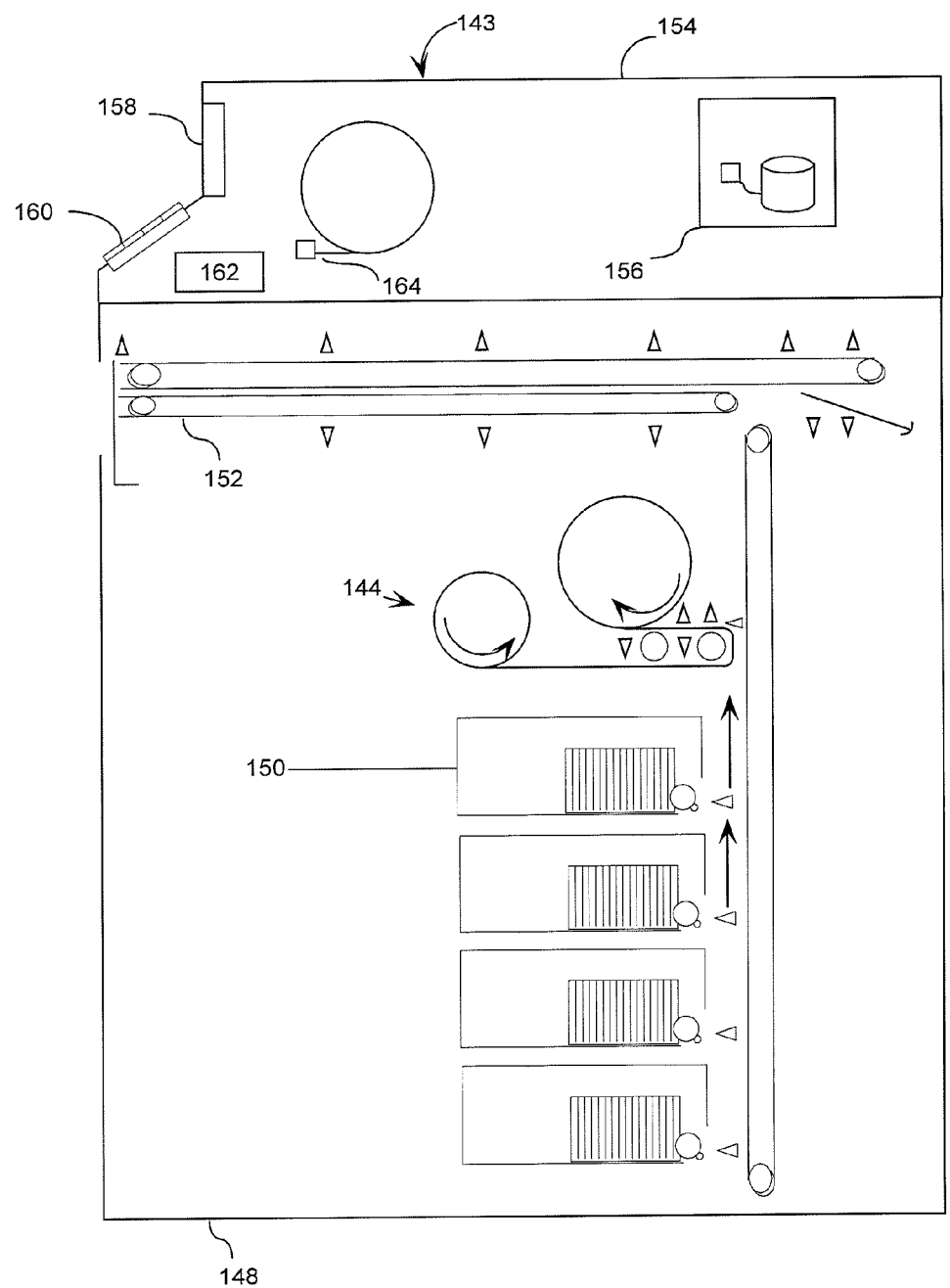
FIGS. 10-12 are schematic views demonstrating operation of the exemplary automated banking machine shown in FIG. 9 in connection with dispensing disinfected items.
Figure 11:
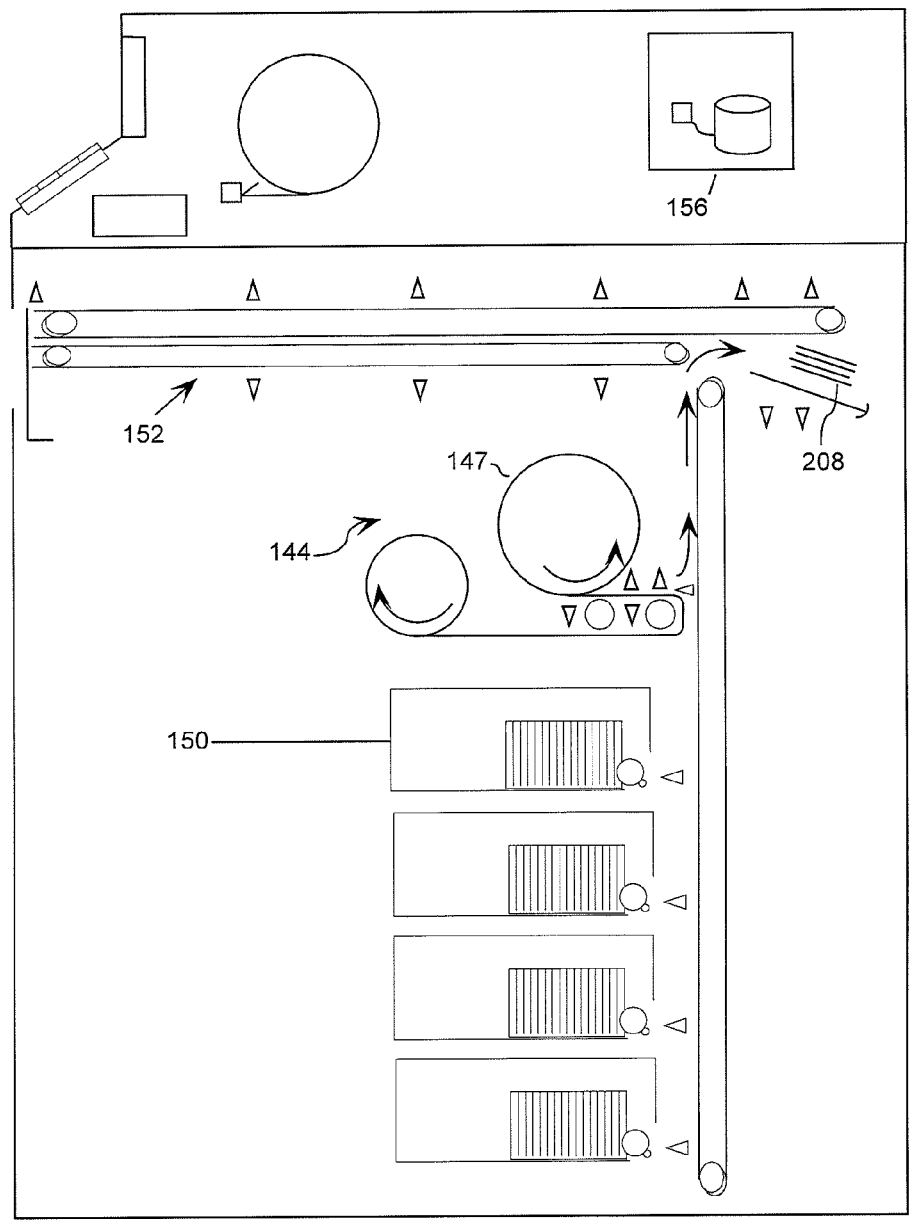
Figure 12:
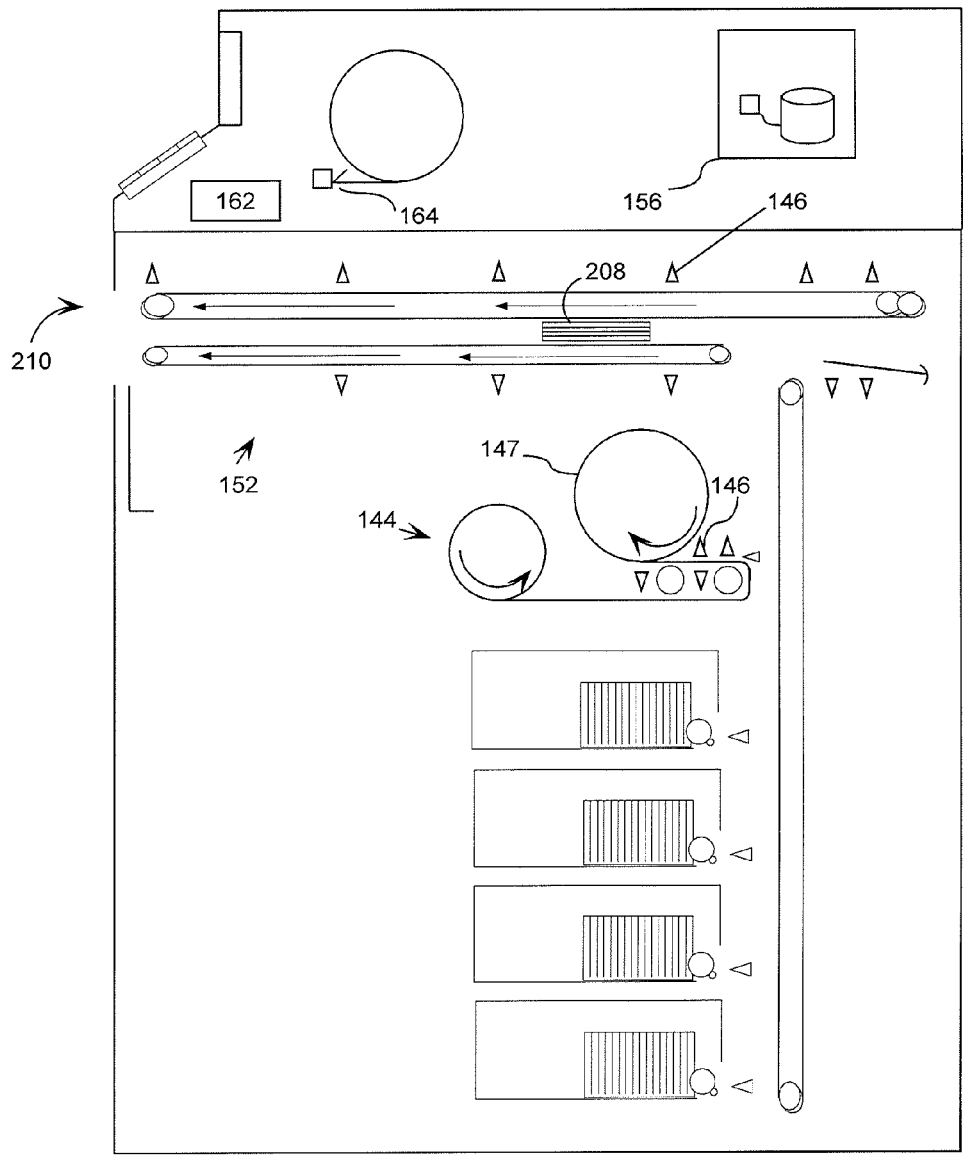
Figure 13:
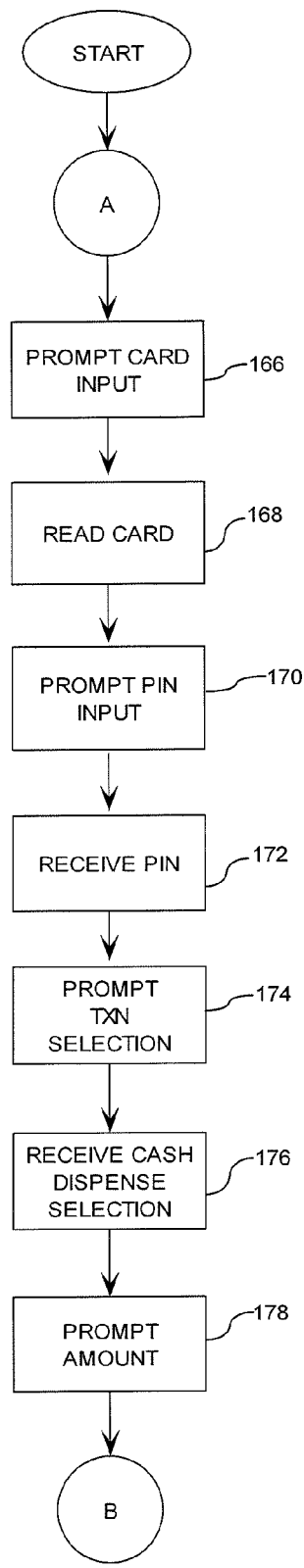
Figure 14:
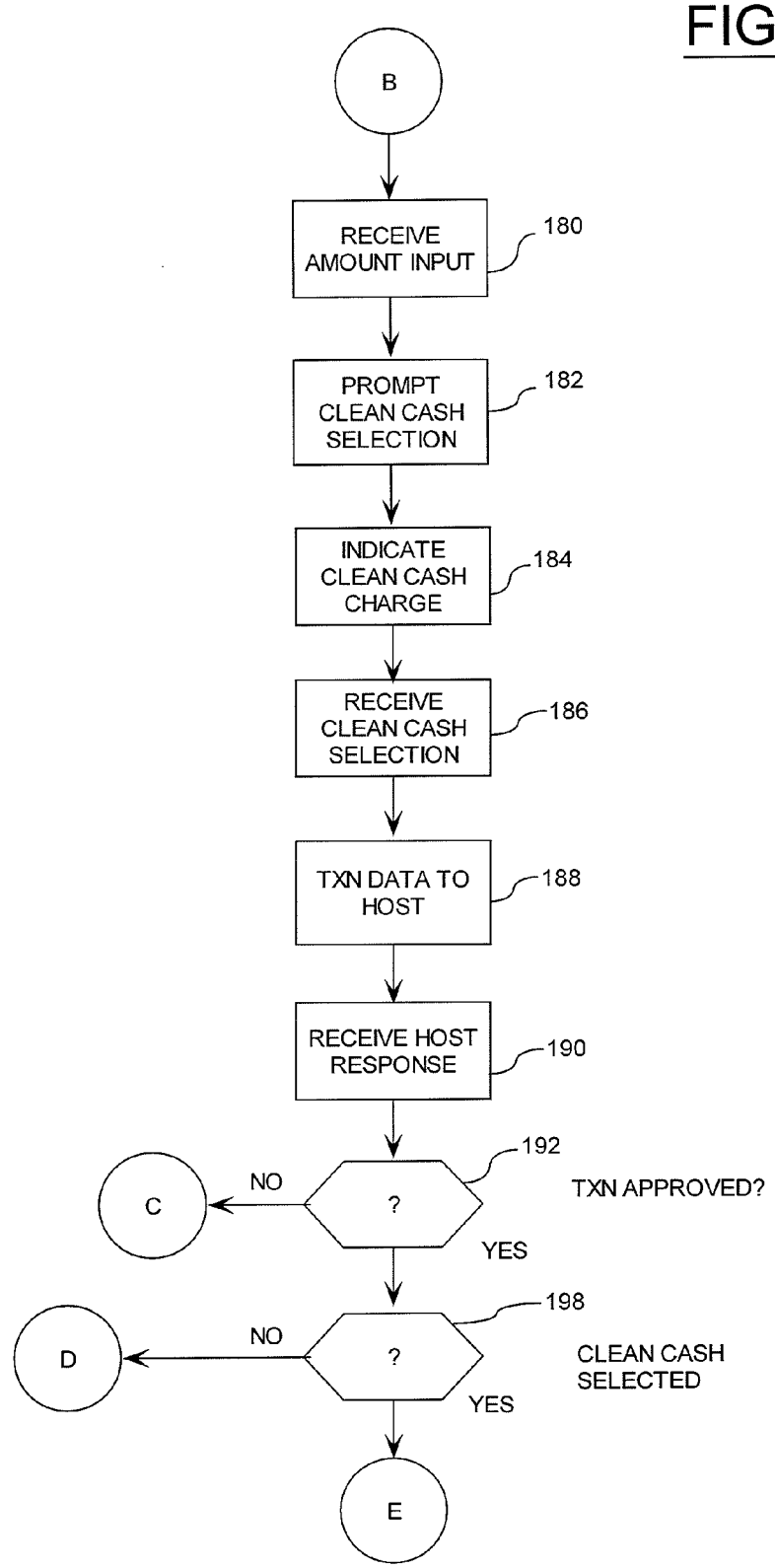

FIGS. 10-12 schematically show certain components of exemplary automated banking machine 143. In the exemplary arrangement the automated banking machine includes a lower chest portion 148. Chest portion 148 includes bill dispenser mechanisms 150. The exemplary bill dispenser mechanisms 150 may operate to selectively dispense currency bills that are stored in the machine and deliver them to machine users through a presenter 152. The bill dispenser mechanisms include features of the type shown in U.S. Pat. No. 7,780,073, the disclosure of which is incorporated herein by reference in its entirety. In other exemplary arrangements the bill dispenser mechanisms may include bill recycler mechanisms. These may include mechanisms that both receive and store currency bills and also selectively dispense currency bills from storage. These currency recycler mechanisms may operate in the manner of incorporated disclosures, including U.S. Pat. Nos. 6,331,000 and 8,356,748, the disclosures of each of which are incorporated herein by reference in their entirety. Further in some exemplary arrangements the automated banking machine may include some mechanisms that are suitable only for dispensing sheets from storage, while others are usable to both receive and store as well as dispense sheets. The particular configuration utilized will depend on the particular requirements of the machine. Further in the exemplary arrangement the chest 148 houses the belt type recycler mechanism of the exemplary arrangement 144. Of course it should be understood that the exemplary embodiments include actuators, controllers, sensors and many other mechanisms not specifically shown that enable the machine to carry out the functions that are hereinafter described.

The exemplary automated banking machine 143 further includes a top housing portion 154. The top housing portion 154 is positioned above the chest and houses the machine controller 156. The top housing 154 also supports the display 158 and the keypad 160. The exemplary top housing further supports the card reader 162 and the printer 164. The top housing also may support additional devices such as function keys, input devices, output devices, transceivers and other suitable devices for the operation of the machine.

In the exemplary arrangement the automated banking machine 143 is operative to utilize the cleaner/disinfecting devices 146 to produce currency bills that are generally free of bacteria, viruses and other potentially harmful items so as to reduce the risk of disease that may occur from handling such items. This is done in the exemplary embodiment by operating the currency dispenser mechanisms responsive to the at least one controller 156 when the machine is not performing transactions for a user. This is done as represented in FIG. 10 by the machine operating to move currency bills from at least one bill dispenser mechanism 150 into storage on the belt recycler 144. During the exemplary operation the cleaner/disinfecting devices operate so as to irradiate the bills before they are loaded onto storage in the belt recycler device using UV-C emitters. In the exemplary arrangement the bills moving into storage on the bill recycler move in supported connection with sets of transversely staggered belts. These belts which move the bills into engagement with a bill storage roll 147 of the belt recycler are offset so that all of the surface areas of all the bills are irradiated. Further in exemplary arrangements the belts which move the previously irradiated bills include impregnated silver or other substances that are operative to retard the growth of harmful bacteria. Further the roll, tape, or other storage media further includes such substances that will retard and/or prevent the growth of undesirable bacteria and viruses on the currency bills. In this way the machine operates to store a supply of clean, disinfected bills on the storage roll 147 of the bill recycler 144.

Further in some exemplary arrangements the cleaning/disinfecting devices may operate to not only irradiate the bills but also to clean the bills so as to remove undesirable substances. This may include, for example, passing the bills through a cleaning mechanism such as sets of moving brushes or other devices to loosen particulate materials or other materials that are adhering to the bills.

Further in exemplary arrangements a vacuum system may operate to pull and collect the impurities that are dislodged from the bills so as to carry the impurities away from the bill surfaces. Such systems may be used for example to remove residues of narcotics that may be present on the surfaces of bills that have been passed by persons who use or deal in illegal drugs. This may avoid, for example, persons receiving from the machine currency bills that may cause drug sniffing dogs or other narcotics sensing systems to be triggered from the use of the particular bills. Of course it should be appreciated that additional or alternative methods for cleansing bills and disinfecting bills may be used. This may depend on the quality of the particular bills. For example in some countries where plastic currency notes are used, certain solvent or other cleaning materials may be appropriate for use in connection with disinfecting such bills that would not be appropriate for use in connection with paper or cloth bills. Alternatively in some arrangements heating or cooling devices may change the temperature of bills to kill undesirable organisms. Of course the particular type of cleaner/disinfecting devices included in the automated banking machine will depend on a number of different circumstances that are involved and the particular substances and organic material that is desired to be removed or neutralized.

The exemplary embodiment of the automated banking machine may be operated responsive to programmable instructions stored in the one or more data stores associated with controller 156. The exemplary logic flow carried out by machine 143 is represented in FIGS. 13-17. In operation of the exemplary machine, the user may be prompted through an initial display screen output to input their user card to the card reader of the machine. This is represented in step 166. The controller 156 in the machine operates to cause the card reader to read data from the card that is usable to identify the financial account. This is represented in the step 168. The controller then operates in accordance with its programming to output through the display a prompt message which instructs the user to input their personal identification number (PIN). This is represented in a step 170. The controller then operates to receive the user input of the PIN through the keypad in a step 172.

The controller 156 then operates to cause the display to output at least one screen that prompts the user to make a transaction selection. This may include a step that presents the user with a display prompt to select a particular account on which their transaction is to be conducted, such as checking or savings. This is represented in a step 174. For purposes of this example, it will be assumed that the user requests the transaction that includes a dispense of cash from the machine. The controller operates to receive the user's input request to receive cash through one or more input devices. This is represented in a step 176. Once the user has input their selection to receive a cash dispense, the controller operates to provide at least one output through the display that prompts the user to input the amount of cash they wish to have dispensed. This is represented in step 178. The controller then operates to receive the user input amount through a user input device on the machine. This is represented in a step 180.

In the exemplary arrangement the program steps stored in the at least one data store associated with controller 156 include data that enables the controller to output a display that prompts a user to provide at least one input concerning whether they wish to receive clean and disinfected cash from the machine. This is represented in a step 182. The machine also provides at least one output that indicates to a user that a charge will be assessed for receiving clean and disinfected cash from the machine. This is represented in a step 184. Steps 182 and 184 may be combined as a single step. In response to these outputs, the machine operates to receive at least one input from the user which indicates whether they wish to receive clean and disinfected cash from the machine or not. The receipt of this indicating input is represented in the step 186.

After receiving the input from the user concerning whether they wish to receive disinfected and cleaned cash, the at least one controller 156 operates in accordance with its programming to send the transaction data associated with the user selected transaction to the remote host computer. This is represented by step 188. The host computer of the exemplary embodiment operates in a manner like that previously described to obtain a determination whether the transaction is authorized or not. It should be appreciated that in this exemplary embodiment the user has selected to receive cleaned cash from the machine. The associated surcharge associated with receiving the cleaned cash will be included in the amount to be assessed to a user's account if the transaction is approved. If the user has not elected to receive cleaned and disinfected cash from the machine, the surcharge is not included in the transaction data sent to the host concerning the amount of the transaction. Of course it should be understood that this approach is exemplary and other approaches, such as independently assessing the surcharge fee through separate machine communications with the host or another computer (e.g., a remote server), may alternatively be used.

As represented in a step 190, the automated banking machine receives a response from the host which indicates whether the transaction is approved or not approved. The at least one controller operates responsive to the received host message in a step 192. If the transaction is not approved, the at least one controller 156 operates to cause the display to provide an output that the transaction has been denied. This is represented in a step 194. The controller also operates to return the user's card in a step 196 and returns the machine to a wait state for the next transaction.

If in step 192 the transaction is indicated to be approved, the at least one controller 156 then makes a determination whether the user has elected to receive cleaned and disinfected cash from the machine. This is indicated in a step 198. If the user has not elected to receive cleaned and disinfected cash from the machine, the at least one controller operates in accordance with its programming to dispense the cash from the bill dispensing mechanisms 150. This cash has not been cleaned or disinfected through operation of the machine. This is represented by a step 200. The machine is operated to dispense the cash to the user and provide (e.g., print) a receipt as reflected in step 202. The controller then operates the machine in step 204 to cause the card reader to return the card to the user. The controller 156 then operates to notify the host that the cash was successfully dispensed to the user so that the host or other connected server may assess the user's account for the value of the cash dispensed. This is represented in a step 206.

In the exemplary embodiment if the user has elected in step 198 to receive quality cash (e.g., uncirculated, new, cleaned, and/or disinfected cash), then the at least one controller operates at step 212 (in FIG. 17) to cause the quality cash stored in the recycler 144 to be dispensed to the user. This is accomplished by the controller operating to remove bills from the storage roll of the belt recycler 144 and to stack the clean bills in a stack 208 of the presenter 152, as shown in FIG. 11. Once the stack of cleaned and disinfected currency bills has been built in the presenter, the stack 208 is moved through operation of the presenter through a bill outlet opening 210 from which the bill stack may be taken by the user. This is represented in FIG. 12. In some exemplary embodiments the bill cleaning and disinfecting devices such as ultraviolet emitters or other irradiation devices may operate during the time period when the bills are being delivered from the belt recycler 144 and to the presenter. Further UV disinfecting devices and other devices 146 may be operated in various other locations in the machine to help assure that the bills which have been disinfected do not attract contaminants as they are moved from the belt recycler to the user. Of course this approach is exemplary and in other embodiments, other approaches may be used.

As represented in FIG. 17, the machine operates to dispense the cleaned and disinfected cash to the user from the machine as represented in step 212. Thereafter the machine operates in accordance with its programming to provide (e.g., print) a receipt for the user as represented in step 214. The at least one controller 156 then operates to cause the card reader to return the card to the user in a step 216. The controller then operates to notify the host computer that the cash was dispensed successfully from the machine. This is represented in a step 218. As previously explained, the messages from the automated banking machine cause the host to assess the user's account for the value of the cash dispensed including the surcharge for the user receiving the cleaned and disinfected cash. Further in this exemplary arrangement the at least one controller 156 operates in accordance with its programming to then (if determined necessary) replenish the supply of cleaned and disinfected cash stored in the recycling mechanism 144. This is done in the manner previously described by moving currency bills from the dispensers 150 into the storage roll of the recycler 144. This is represented by a step 220. Of course it should be understood that these transaction flows are exemplary and in other automated banking machine arrangements, other or alternative approaches may be used for providing a user with bills that have been cleansed of potentially harmful or undesirable impurities.

In other exemplary embodiments the machine 143 can operate to analyze the quality of currency notes stored in the cash dispenser 150. For example, during a cash reloading process the cash dispenser 150 is supplied with currency notes. The added currency notes may be inside currency cassettes that get inserted into the cash dispenser 150. The controller is programmed to cause notes to be removed from these currency cassettes and then moved past a note analyzer, which can measure several factors of note quality. The note analyzer can be used to determine whether a note is of high quality. For example, a high quality note may not need to be cleaned and/or disinfected. As a result, a high quality note can be directly placed (without cleaning) onto a storage roll of the recycler 144. Of course notes determined to be of high quality may also be thoroughly cleaned before being stored onto a storage roll of the recycler 144.

In another exemplary embodiment a designated portion of the cash dispenser 150 includes currency cassettes that hold uncirculated (brand new) currency notes. That is, these notes have never been in public circulation. Thus, these notes should be relatively free of any dirt, disease, germs, viruses, harmful bacteria, etc. The controller is operable to maintain a real time count of the quantity of uncirculated notes (and their respective denominations) that are available to be dispensed by the machine. Uncirculated notes can be dispensed to user for an extra fee. The fee assessed to a user can vary. For example, the extra fee may be on a per note basis, a single fee for a specific quantity of notes (e.g., three notes), or a single fee for the entire cash dispense, etc. The uncirculated note fee may be waived for select users, such as VIP customers. Also, some machine users may be permitted the option to withdraw more uncirculated notes than other users.

The uncirculated notes stored in the machine may also be of higher denominational value than regular (unclean) notes stored in the machine. For example, an uncirculated note may be a $50 and/or a $100 bill, whereas a regular note may be a $20 bill. As can be appreciated, the arrangements allow a user of an automated banking machine (e.g., an ATM) the ability to easily obtain an uncirculated note, such for use as a gift.

Figure 24:
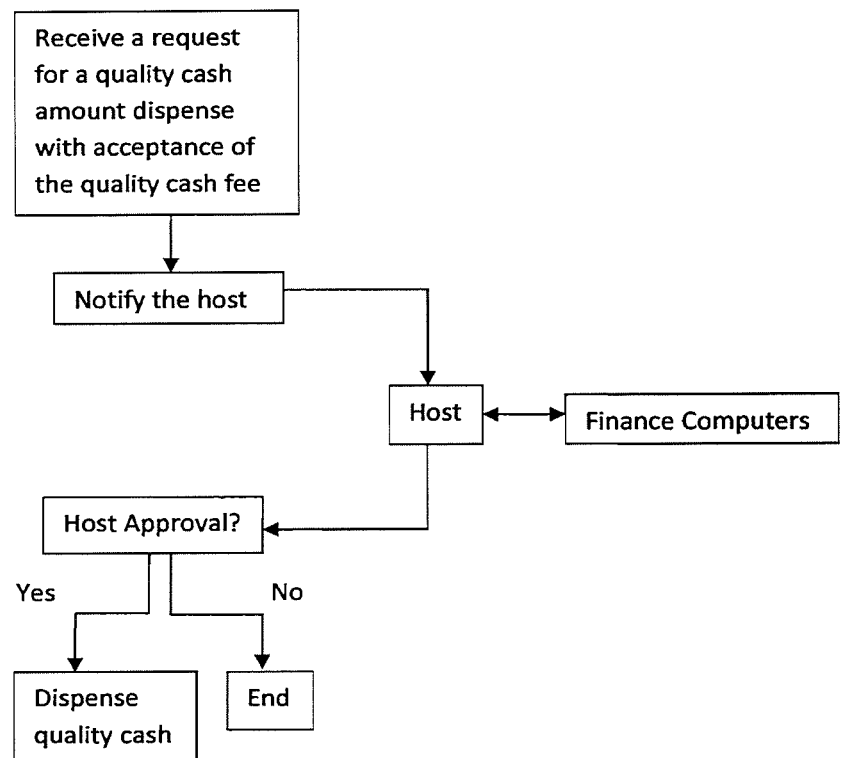
FIGS. 24-27 are schematic representations of steps carried out by logic flow associated with automated banking machine transactions involving quality cash.

FIG. 24 shows a further exemplary programming logic flow that can be carried out by the machine 143. As can be seen, the machine can receive a user request for a cash withdrawal transaction which includes quality cash and user acceptance of the extra quality cash fee. The machine sends a transaction authorization request to the host. The authorization request includes the cash withdraw amount and the extra fee amount. The amounts are presented to the host to be assessed against the user's account. The amounts may be combined by the machine into a single total value that is presented to the host. Upon host approval of the transaction, the machine operates to dispense the requested amount of quality cash. Upon host disapproval of the transaction, the machine operates to notify the user that the transaction request is denied, which may include ending the user session with the machine.

Figure 25:
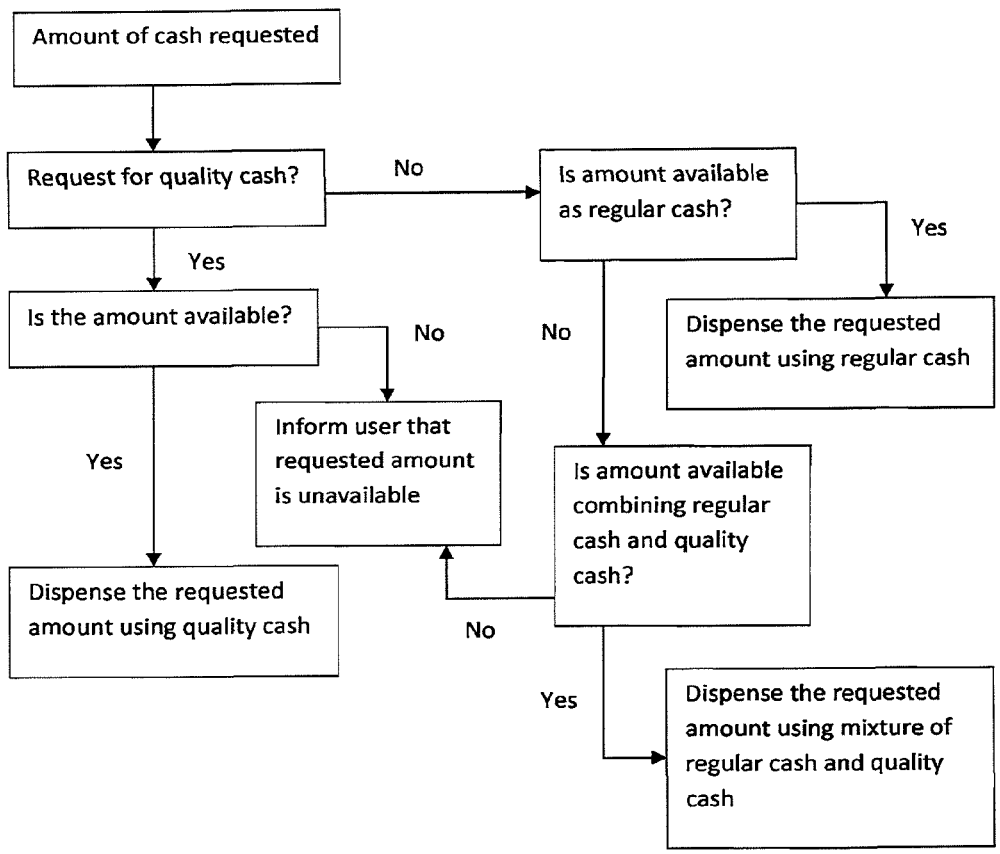

FIG. 25 shows a further exemplary programming logic flow that can be carried out by the machine 143. As can be seen, the machine can determine the real time quantity and denomination of both clean (quality) and unclean (regular) notes currently available to be dispensed.

The machine can compare a requested amount of quality cash to the amount of quality cash currently available. If available, then the total amount of quality cash can be dispensed. Otherwise the user can be informed that the requested amount of quality cash is unavailable. The logic flow may then lead the user back to a screen where a smaller amount of quality cash can be requested. For example, the machine may notify the user of the total amount of quality cash available to the user. The machine may also provide the user an option to mix regular notes with quality cash to meet the total cash withdrawal amount. The logic flow may eventually lead the user back to a screen where a regular cash dispense can be requested.

The machine can also compare a requested amount of regular cash to the amount of regular cash currently available. If available, then the total amount of regular cash can be dispensed. Otherwise the user can be informed that the requested amount of regular cash is unavailable. Alternatively, the machine logic flow may try to meet the requested total cash withdrawal amount by mixing the available regular notes with some quality cash (e.g., a small amount, such as one note). The user would not be charged a fee for receiving the quality cash.

Figure 26:
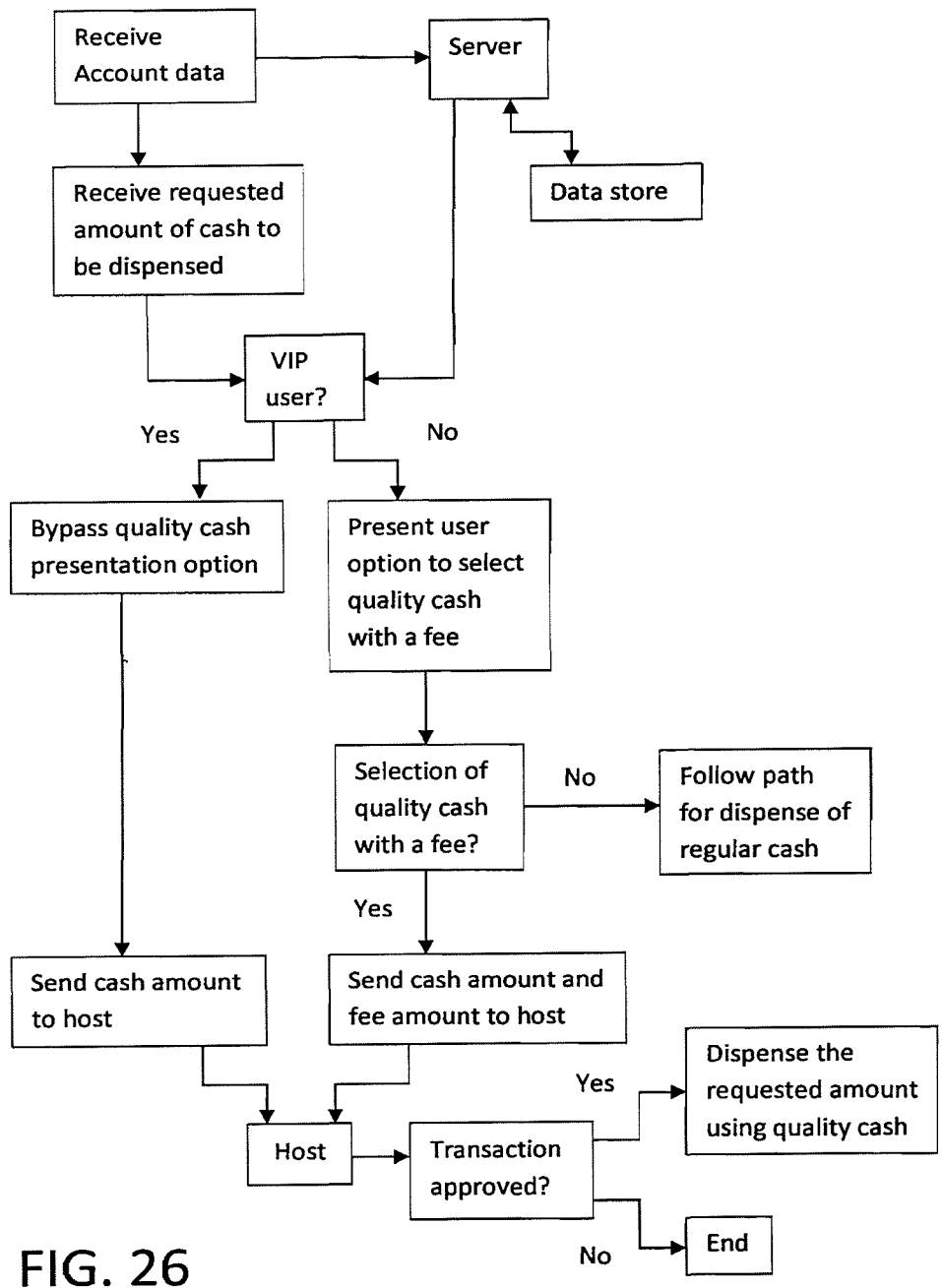

FIG. 26 shows a further exemplary programming logic flow that can be carried out by the machine 143. As can be seen, the machine can communicate with a server to determine whether the current user is in a special program (e.g., a VIP user). The machine-to-server communication is independent of the transaction host. That is, the machine can (directly) communicate with the server without involving the host in the communication path.

The machine sends user data (e.g., account data or other user identifying data) to the server. The server operates to determine whether the user data corresponds to VIP user data. The server can access a data store that includes the VIP user data for a plurality of users that are to automatically receive quality cash. Depending on the VIP program, the user may or may not be assessed the extra fee. As can be seen, if the user is determined to be a VIP then the logic flow causes the machine to bypass presenting the normal user option to select purchasing quality cash. The machine can send a transaction authorization request to the host. Again, the machine has an ability to send an authorization request that does not include the extra fee that is normally assessed to a user account for receiving quality cash.

As can be seen, if the user is determined not to be a VIP then the logic flow causes the machine to present the user option to select purchasing quality cash. If the non VIP user selects to pay the fee to receive quality cash then the machine sends a transaction authorization request to the host that includes the extra fee for receiving quality cash. The extra fee can be assessed to the user's account through operation of the host. As discussed in more detail later, in other embodiments the extra fee can be assessed by use of an independent server instead of the host.

Figure 27:
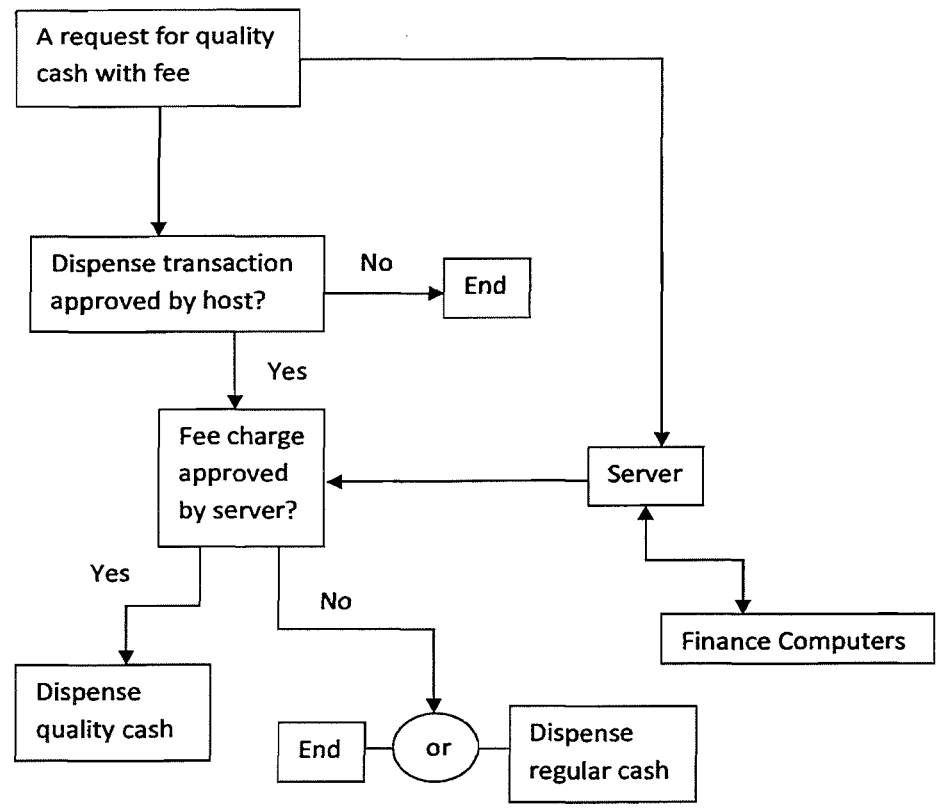

FIG. 27 shows a further exemplary programming logic flow that can be carried out by the machine 143. As can be seen, the machine can independently communicate with a server which can assess the extra fee associated with a quality cash dispense. The charging of the extra fee amount can be a separate financial transaction that is carried out independent of the cash withdrawal transaction. That is, the extra fee transaction can be performed independent of host involvement. The host can still handle (and approve) the cash withdrawal transaction.

As shown, user data (e.g., a user account number or data usable to determine a user or an account) can be sent from the machine to the server. The server can communicate with one or more financial computers to determine whether the user account can cover (is good for) the extra fee. The server may assess (debit or charge) the fee at this time in the logic flow or may wait until later receiving a confirmation message from the machine that the amount of quality cash was properly dispensed from the machine. The server notifies the machine of the determination. Upon receiving a fee approval message from the server, the machine operates to carry out the dispense of the requested amount of quality cash. However, upon receiving a disapproval message from the server the machine operates to either end the user session or allow the user an option to request a cash withdrawal involving regular cash. It should be understood the steps shown are exemplary, and in other embodiments other arrangements of the steps can be used. For example, the machine may be notified of the server's determination regarding the extra fee assessment before the machine sends the transaction authorization request message to the host for approval of the cash withdrawal transaction. Again, the machine logic flow allows for both one transaction portion carried out through machine-to-host communication and another transaction portion carried out through machine-to-server communication. Each communication portion can be independent of the other.

It should be understood that the logic flows shown in FIGS. 24-27 are exemplary. That is, in other automated banking machine logic flow arrangements, other or alternative approaches or programming may be used for providing a user with quality cash. Likewise, other or alternative approaches or programming may be used for assessing (if necessary) the extra fee.

Figure 19:
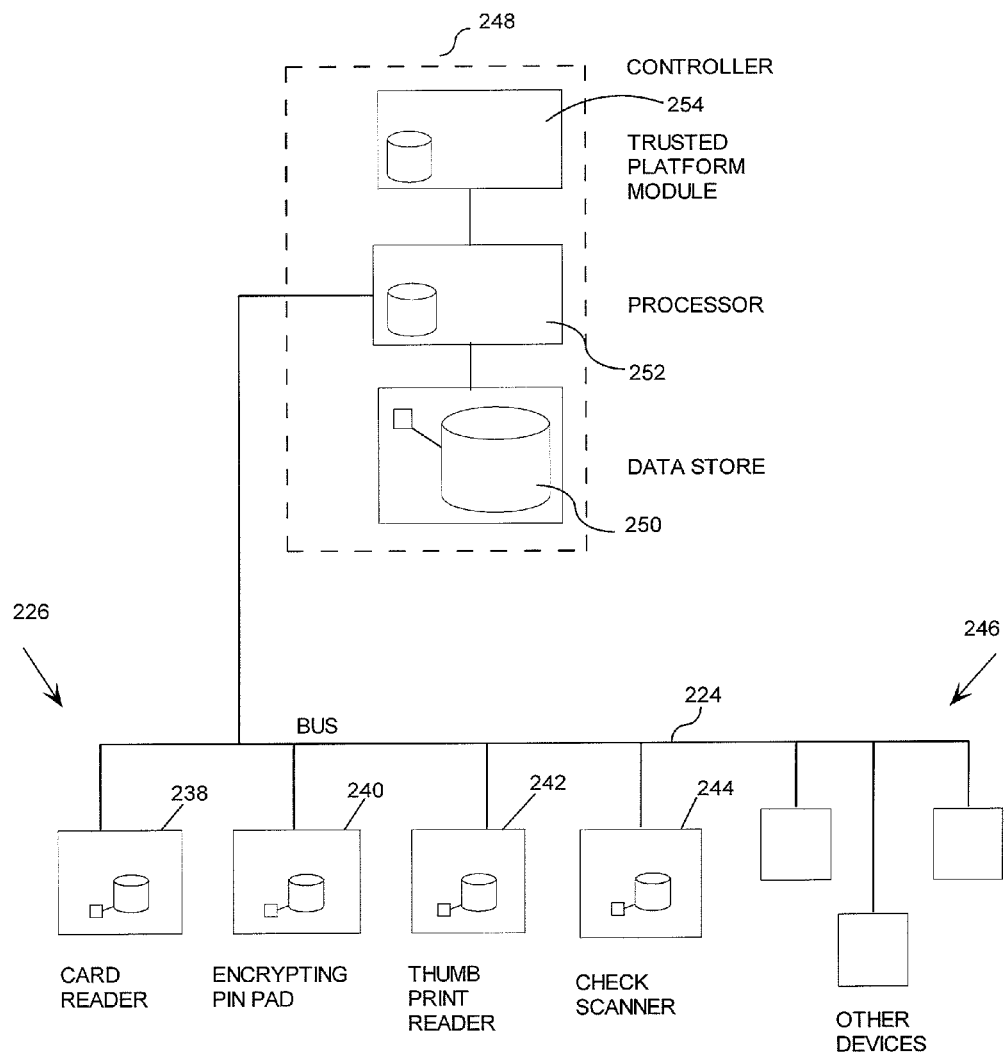
FIG. 19 is a schematic view of a controller and devices used in an exemplary automated banking machine.

FIGS. 18 and 19 represent the software and controller architecture associated with an alternative exemplary automated banking machine. As can be appreciated in exemplary embodiments the controller includes circuitry which has one or more processors that execute computer executable instructions. Computer executable instructions corresponding to various types of computer programs are stored in the at least one data store associated with the processor. These computer executable instructions when executed cause the machine to operate to carry out the transaction functions such as the functions previously described.

The exemplary computer executable instructions include a number of different software programs. These software programs as represented in FIG. 18 may include an operating system schematically indicated 222. Operating system 222 may include, for example, a Windows® operating system, a Linux operating system, a Chrome operating system or other suitable operating system for the particular environment in which the processor and associated software operate. The operating system also communicates via a communications bus schematically indicated 224. Communications bus 224 may include a proprietary or non-proprietary communications bus such as for example a Universal Serial Bus communications architecture that is suitable for communicating with transaction function devices generally indicated 226, which are later described in detail. The exemplary software architecture includes a plurality of device drivers schematically indicated 228. Device drivers 228 provide an electronic communication interface to the transaction function devices 226. In the exemplary arrangement specific device drivers for each particular transaction function device are included in the software architecture.

In the exemplary arrangement the device drivers 228 are in operative communication with an XFS interface 230. The XFS interface may in some exemplary arrangements comprise a device interface layer that meets the requirements of the CEN Extensions for Financial Services (XFS) Standard. This Standard provides a standardized software interface for numerous different types of devices that are used in financial systems. By including an XFS interface the exemplary software architecture provides a standardized software interface to which different software developers may interface their machine operating software applications. This is possible because the communications that are necessary to operate and receive data from the devices are presented in a standardized format which is available to application developers. Of course this approach is exemplary.

Further in the exemplary software architecture a software application 232 is included. In the exemplary embodiment the software application includes the computer executable instructions that are executed by the at least one processor of the at least one controller to cause the machine to carry out the transaction functions of the machine. In exemplary arrangements the application software is what causes the machine to perform the necessary activities and to operate the various devices so as to enable the machine to carry out the various types of financial transactions of which it is capable.

The exemplary software architecture further includes some other programs including security software programs represented 234. The security software 234 may include types of software that are suitable for the particular type of automated banking machine. Such security software may include, for example, firewall software that prevents the machine from connecting to unauthorized network addresses. Security software may also include software that is usable to identify viruses or other exploits that might execute on the machine. The security software may also include software that operates to enable security features of the machine and provide secure communications of the type hereinafter described. The exemplary software architecture further includes certain utilities schematically represented 236. Utility software may include, for example, software that is needed to perform ancillary functions associated with the machine. This may include, for example, software that keeps track of currency stored in the machine so that the machine can report its current status to one or more remote computers. The utility software may also include in some arrangements predictive maintenance software which monitors aspects of machine operation and reports conditions that are likely to need attention in the near future. This may include potential device failures, replenishment of supplies such as paper, cash or other things that will likely need to be done to the machine. Various types of utility software may be included in the software of the machine depending on the particular type of automated banking machine involved.

As represented in FIG. 18, the exemplary transaction function devices communicate messages through the bus 224 with the controller that includes the representative software stack. The transaction function devices in the exemplary arrangement include a card reader 238. Another transaction function device of the exemplary arrangement includes an encrypting PIN pad 240. A thumbprint reader 242 which is an input device usable to receive identifying inputs from users is also included in this exemplary arrangement. As schematically represented each of the devices 238, 240 and 242 include one or more circuits which have respective processors and data stores. The circuits are capable of carrying out computer executable instructions stored in their respective data stores to enable these devices to not only carry out functions but also to provide security features in a manner hereinafter discussed.

Another exemplary transaction function device that is included in this automated banking machine is a check scanner 244. Check scanner 244 operates to produce images of financial checks that are received through the check scanner. The check scanner also includes circuitry which includes at least one processor and at least one data store as schematically represented. Check scanners and other devices used in exemplary arrangements may include features like those described in U.S. Pat. Nos. 8,418,916; 7,922,098; 7,837,096; 7,815,104; and/or 7,595,816 the disclosures of each of which are incorporated herein by reference in their entirety. In addition numerous other types of devices generally referred to as 246 may be included in the machine. Devices 246 may be of the types previously described such as displays, portals, output devices, input devices, sensing devices or other types of devices that may be included in the machine. Of course additional or different devices may be included in various embodiments.

Shown in FIG. 19, the software components referred to in FIG. 18 are executed in a controller 248 of the exemplary machine. The controller includes one or more circuits that include one or more data stores schematically indicated 250. Data store 250 of the exemplary embodiment may include a processor controlled hard drive or other suitable data storage unit that is controlled through operation of at least one associated processor. The control circuitry of the exemplary embodiment further includes at least one processor schematically indicated 252. The processor 252 may include a microprocessor, an Intel iCore processor or other suitable processor that is capable of executing the instructions stored in the at least one data store.

The exemplary controller further includes a trusted platform module (TPM) schematically represented 254. The trusted platform module of the exemplary embodiment operates in accordance with programmed instructions and provides a security device to reduce the risk of unauthorized devices operating in the machine. Further the trusted platform module may also be used to assure that the devices which operate in the machine have not had their software programming modified from documented secure programming conditions. Such changes in software in the devices may result from attempts to conduct exploits on the machine. Further in exemplary arrangements the trusted platform module may operate to provide secure communication between the controller and one or more of the transaction function devices in the machine. Exemplary embodiments may include features like those described in the following U.S. Patents, the disclosures of which are incorporated herein by reference in their entirety: U.S. Pat. Nos. 8,474,698; 8,342,395; 7,988,039; 8,448,850; 7,967,193; 8,100,323; 8,052,048; 8,052,047; 8,038,057; 7,988,039; and 7,229,009. Of course it should be appreciated that although in some exemplary arrangements the trusted platform module is utilized to provide secure communications and secure operation of the controller and the associated devices, in other arrangements other hardware and software may be utilized to accomplish these functions.

In exemplary embodiments the software architecture operates to avoid possible security problems that might otherwise arise due to compliance with the CEN XFS Standards, particularly security vulnerabilities are possible due to the required standardized interface between the application and the device drivers, and which requires that certain data that is received through or produced by the transaction function devices must be presented to the application so that the application can carry out the necessary transaction steps. Presenting the data to the application in the required standard and/or unencrypted format may present issues as criminals may be able to intercept the data within the machine at the standardized interface.

In the exemplary arrangement the devices that are enabled to provide secure communication between the devices and the controllers are operated to prevent the transmission of sensitive data through the XFS device interface. This is accomplished by using substitute data which can then be correlated through operation of the originating device with the actual data that is needed for the transaction. Such actual data may then be sent from the device to the controller in a secure and encrypted manner to avoid the unauthorized interception thereof.

In exemplary arrangements a card reader may read card data from the magnetic stripe of a user card. Alternatively or in addition the card reader may operate to read data from a chip of a smart card. This may be done via electrical contacts or via wireless communications. Such data read through operation of the card reader may be caused to be stored in accordance with the programming of the processor associated with the circuitry of the card reader in the at least one data store of the circuitry. In some exemplary arrangements the circuitry of the card reader may operate to cause the card data and/or chip data to be stored in an encrypted manner.

Responsive to the programming of the circuitry of the card reader, instead of sending the card and/or chip data to the XFS interface software layer, the card reader operates to produce substitute data that can be correlated through operation of the circuitry in the card reader with the actual read data from the card. Substitute data produced by the card reader may then be utilized and passed through the XFS interface to the application. The application may be configured to operate to then securely recover the actual card data at an appropriate place in the transaction steps when such data is needed. Alternatively in some arrangements the security software included with the software installed on the machine may operate to determine when the card data is needed and take the necessary steps to cause communication with the card reader to recover the actual data. In the exemplary arrangement when the application calls for the card data, the at least one controller operates in accordance with its programming to communicate securely with the control circuitry in the card reader 238. The application and/or the security software communicates the substitute data to the card reader that then operates in accordance with its programming to recover the actual card data. Such card data can then be recovered from the data store in the card reader and transmitted in a secure and encrypted manner to the application layer or the security layer where the actual card data needed for carrying out the transaction is resolved and utilized for purposes of further carrying out the transaction steps. As can be appreciated, this approach avoids passing the card and/or chip data in a clear and unencrypted manner through the XFS interface.

Similar approaches may be utilized with certain secure input devices such as the exemplary thumbprint reader 242. Again the thumbprint reader may operate in accordance with its programmed control circuitry to provide data that is a substitute for the actual data which is read from the user's thumbprint. Instead the substitute data is utilized by the thumbprint reader to recover the actual data. The controller operates in accordance with the software programming to transfer the substitute data through the XFS software interface to the software application. Again the security related software for the application operates to cause communication with the thumbprint reader so that when the actual data is needed, secure communication of the substitute data is sent to the thumbprint reader. The thumbprint reader then recovers the actual data and transmits it in a secure and encrypted manner to the application which then may utilize it for purposes of carrying out the transaction.

Other exemplary embodiments may include secure operation of the check scanner. The check scanner produces images of checks that are received through operation of the machine. These checks include private data such as the check writer's account number, the check writer's name and address and other information that may present privacy concerns. In exemplary arrangements to minimize the risks associated with transmitting this data and/or images in the clear through a standardized interface, substitute data is generated through operation of the circuitry in the check scanner. The substitute data is then correlated with stored data in the data store of the check scanner. Again as with the other examples the substitute data is processed and passed through the software layers. The substitute data is utilized until the actual data is needed by the application. At the point in the transaction where the actual data is required, secure communication of the substitute data to the check scanner is made. The substitute data is then utilized to recover the actual data which is then sent in an encrypted and secure format to the application. The application can then use this data for purposes of processing the transactions in a manner like that described in the incorporated disclosures. As can be appreciated, numerous applications of these approaches may be utilized in exemplary embodiments to avoid having to store or to pass data in the clear between software applications at the XFS interface. Thus the exemplary embodiment enables the configuration of software architectures in machines in accordance with the XFS standards or other suitable standards but avoids the possible security risks that compliance with such standards may impose. Of course it should be understood that the principles may be utilized in various types of automated banking machine environments to help in providing enhanced security.

Figure 20:
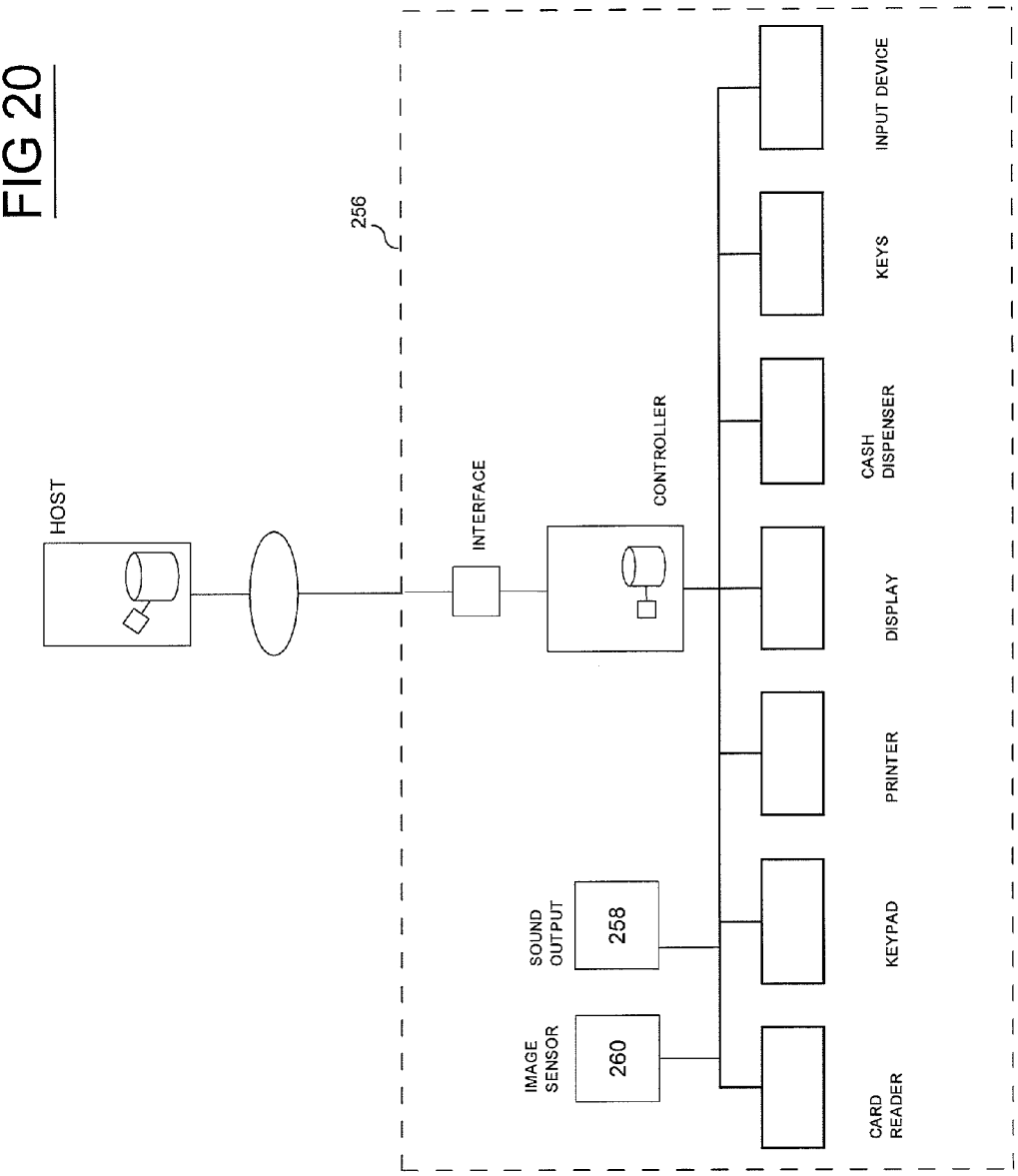
FIG. 20 is a schematic view of components included in an exemplary alternative automated banking machine that has a user interface that facilitates operation by blind or sight impaired users.

FIG. 20 shows yet a further alternative embodiment of an automated banking machine generally indicated 256. Automated banking machine 256 may include devices of the types previously described and may operate in a manner similar to that described in connection with automated banking machine 12 except as hereinafter specifically discussed. Automated banking machine 256 includes improved capabilities for operation of the machine by users that are blind or that have impaired vision. In order to facilitate the operation of the machine by blind or other disabled users, the exemplary machine 256 includes at least one sound output device schematically indicated 258. Sound output device 258 may include devices that are usable to produce audible outputs corresponding to instructions for operation of the machine. Such sound outputs may include in some exemplary embodiments a headphone jack, audio speakers, wireless transmitter or other suitable devices for providing signals which can be directly or indirectly audibly perceived by users and which instruct the user in how to operate the particular machine in the absence of the ability to visually see the output or input devices of the machine. Exemplary machines may include features like those described in the following U.S. Patents, the disclosures of which are each incorporated herein by reference in their entirety: U.S. Pat. Nos. 8,308,057; 8,393,534; 8,469,266; and/or 7,988,041.

The exemplary automated banking machine further includes a user interface having an imaging sensor schematically indicated 260. In exemplary embodiments the imaging sensor 260 may include an active pixel sensor which is operative in accordance with its programming to capture numerous images of adjacent structures in rapid succession so as to determine the direction of movement of an adjacent object. Such imaging sensors may include photo diodes or complimentary metal oxide semiconductor (CMOS) sensors that are operative to detect movement of an adjacent structure. Such imaging sensors and related circuitry which are used in optical computer mice, cameras and other types of devices may be operative to analyze the successive images that are captured from an object and to compare the relative movement between successive images. This enables determining the amount and direction of movement of the adjacent object. This enables providing selected types of inputs to the machine through the detected movement by the imaging sensor. Of course it should be understood that while only one imaging sensor is discussed, multiple imaging sensors may also be utilized for purposes of determining movement and resolving inputs.

Figure 21:
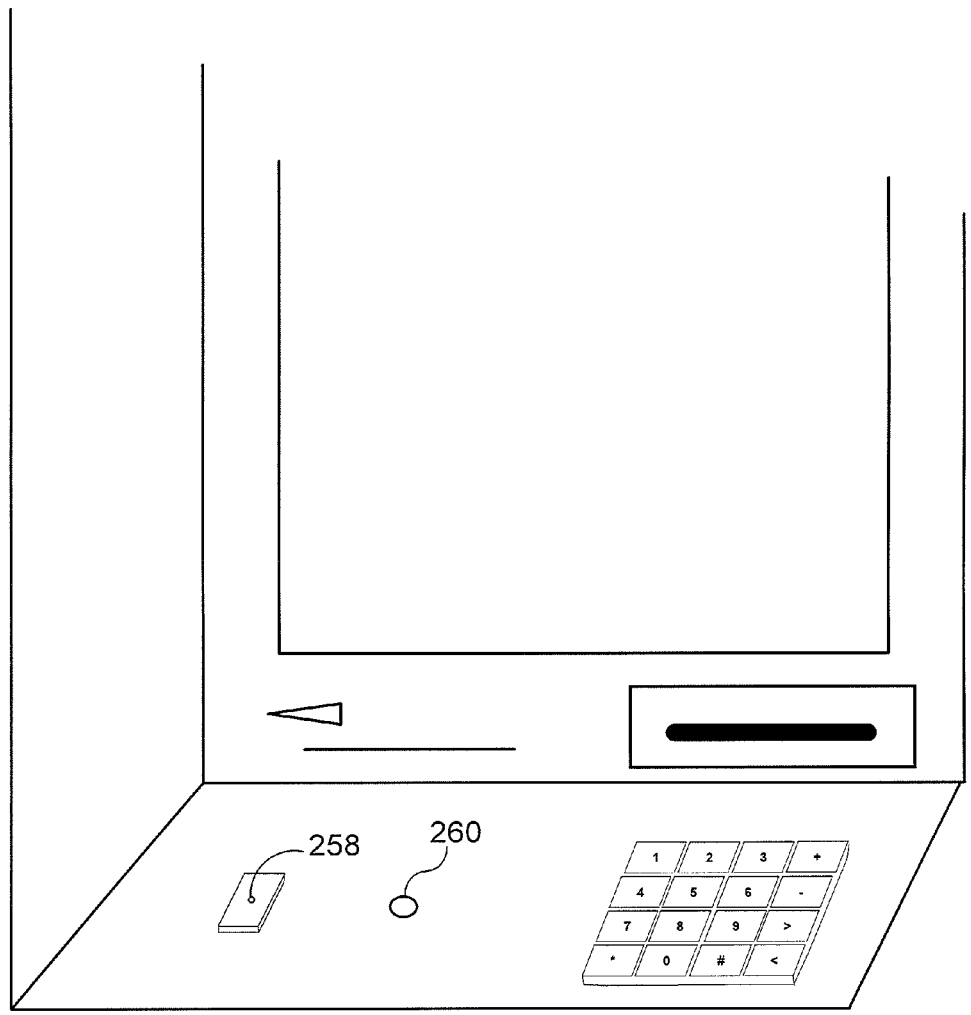
FIGS. 21-23 show different alternative user interface arrangements for an automated banking machine of the type shown in FIG. 20.

In the exemplary arrangement, the one or more imaging sensors 250 is utilized to detect movement of a machine user's body part such as a hand, finger or other body surface to provide inputs to the machine. For example as represented in FIG. 21, the imaging sensor 260 may be placed adjacent to the keypad or other input devices of the machine. As represented in FIG. 21, the user interface of the automated banking machine includes a sound output device in the form of a headphone jack. In the exemplary embodiment the at least one controller operates in accordance with its programming to provide output instructions to the user and to receive inputs based on movement of a user's hand adjacent to the imaging sensor.

For example in the exemplary arrangement shown in FIG. 21, the controller may operate in accordance with its programming and a suitable interface circuit to detect the insertion of a headphone connector into the headphone jack 258. Responsive to detecting this connection, the controller may provide outputs that produce audible signals in the headphones that advise the user to move their hand in an area of the machine to the right of the headphone jack. The exemplary controller may then operate in accordance with its programmed instructions to produce audible outputs that advise the user to move their hand to the right if they wish to increase headphone volume or to the left if they wish to decrease volume. The controller may then sense movement of the user's hand to the right or the left through operation of the imaging sensor 260 and cause the associated circuitry to adjust the volume output accordingly.

In an exemplary arrangement the user may then be instructed to move their hand in a direction away from the machine if the wish to blank the display of the machine during their transaction. The controller upon sensing through operation of the imaging sensor that the user has moved their hand in a direction away from the machine, operates to cause the display to go blank or otherwise display indicia that is not related to the user's transaction. If the user's hand is not sensed as moving away from the machine, the display continues to operate in a manner similar to that utilized when the machine is operated by users with normal vision.

In the exemplary arrangement the controller may operate in accordance with its programming to then provide audible outputs to the user indicating that the card accepting slot is positioned approximately ten inches to the right, and two inches above where the user's hand is currently sensed. The user may then move their hand to the card reader slot and input their card. The controller then operates in accordance with its programming to sense that the card has been inserted and then operate the card reader to read the data from the user's card.

Upon determining that the user's card has been read, the controller may operate in accordance with its programming to indicate to the user that they can input their PIN number through a keypad that is located eight inches to the right of the headphone jack. The user may then locate the keys on the keypad to provide their PIN input. Generally one or more keys of the keypad may include an indicator so that the user can locate a particular key. For example in some arrangements the "5" key of the keypad may include a raised dimple which facilitates a blind user finding the central 5 key of the keypad. The user may then input their PIN in this manner.

Alternatively in some arrangements the programming of the controller may cause audible outputs that instruct the user to move their hand in certain ways to provide a selected PIN input. For example the controller may operate to advise the user to move their hand in the area of the sensor to the left and then to the right to start audible outputs corresponding to a series of digits. The user may be instructed to move their hand toward the machine when they hear a digit that they wish to input. The controller may then operate in accordance with its programming to provide audible outputs of the series of numerals until the user moves their hand in the manner which indicates that they have selected that particular output digit. The user may then be advised that they have selected the particular digit and to move their hand in a certain way if they would like to select a second digit by having the machine output a series of numerals and to again move their hand in a particular way when they want to select a second digit of their PIN. This process may be repeated until the user has provided all of their PIN digit inputs. Of course it should be understood that this approach is exemplary and in other embodiments, other approaches may be used.

In exemplary arrangements the controller may then operate in accordance with its programming to provide audible outputs to the user to have them select a particular type of transaction. This may be done in some arrangements such as those described in the incorporated disclosures by having the user provide inputs through the keypad. In this manner the user may select the type of transaction they wish to conduct in the machine. For example the user may provide key inputs to select balance inquiry, a cash withdrawal, a deposit transaction, a check accepting transaction or other transactions that are available through operation of the machine. The user can then provide the appropriate key inputs to select their desired transaction.

Alternatively in some embodiments the controller 176 may operate in accordance with its associated programming to instruct the user to move their hand in certain ways adjacent to the imaging sensor to make selections. For example the user may be instructed to move their hand to the left to select a balance inquiry and to the right to select a cash withdrawal. A user may be further instructed to move their hand toward the machine to select a deposit transaction and away from the machine to select a check cashing transaction. Further for additional transactions, additional types of movements or series of movements may be indicated through audible instructions to the user so that the user may select their transaction by moving their hand a certain way or through a series of movements. After the controller has determined that the user has moved their hand a certain way, the user may be given the option to indicate that they agree that that is their selected transaction by moving their hand one way, or to reset and select a different transaction by moving their hand an opposite way. Of course these approaches are exemplary.

In exemplary embodiments the user once they have selected a transaction type, is instructed to enter an amount associated with the transaction. For example in cases of cash withdrawal, the user may be instructed to enter the amount of cash they wish to receive through the keypad. The user may be instructed in the manner of the incorporated disclosures to provide their input amount through the keypad and then provide a further input confirming the amount. Alternatively the user may be instructed to provide an input through the keypad the amount associated with a deposit, a check cashing transaction or other transaction that involves a financial transfer. Audible outputs produced through operation of the exemplary controller may advise the user of the selected input and ask them to provide a further input to confirm the amount selected.

Alternatively in other arrangements the controller may operate in accordance with its programming to cause audible outputs to be presented that enable the user to select an amount associated with their transaction through hand movements adjacent to the imaging sensor. For example the audible outputs may instruct the user to move their hand a certain way to indicate the first digit of the amount that they wish to receive. As the user moves their hand in the particular direction instructed, the amount may increment to the desired first digit. When the user stops moving their hand, the machine controller may operate in accordance with its programming to indicate that the user has selected the first digit. Thereafter the controller may operate in accordance with its programming to instruct the user to select a second digit. The controller may operate in this manner until the user has selected all of the digits of their selected transaction through hand movements. Further once the digits have been selected, the controller may prompt the user to move their hand adjacent to the imaging sensor in a certain way to confirm the amount that they have selected. In exemplary embodiments the controller may operate in accordance with its programming after it has received the necessary transaction data to instruct the user to provide at least one input which is indicative that the user wants to proceed with the transaction. The controller may operate in accordance with its programming to indicate the transaction type and amount that the user has selected. The user may then be instructed to provide a particular input to confirm the transaction should proceed. This may be done for example by the user providing at least one input through an input device such as the keypad. Alternatively the at least one controller may operate to advise the user to move their hand in a certain way adjacent to the imaging sensor in order to indicate that they wish to proceed with the transaction.

Once the user has provided the confirming input, the automated banking machine operates to then provide the particular transaction functions through operation of the devices. For example if a user has requested a cash withdrawal transaction, the controller operates the cash dispenser to make the cash available to the user. The controller then operates to indicate through audible outputs to the user where to place their hand to take the cash. For example the controller may indicate to the user that they may take the cash through the cash dispensing slot that is located six inches to the right and five inches below the headphone jack.

In exemplary arrangements the controller may then operate after the user has taken their cash to ask whether they wish to conduct another transaction or end the session. Again in exemplary embodiments the controller may operate in accordance with its programming to accept inputs either through the keypad or other input devices or by sensing hand movements through the imaging sensor. If a user requests another transaction, the controller may operate in accordance with its programming to instruct the user how to provide the inputs to identify the transaction type and the amount. Alternatively if the user wishes to terminate the transaction session, the controller will provide audible outputs to indicate to the user where to position their hand to take their card, printed receipt and to perform other actions the user should take. As can be appreciated, exemplary embodiments may enable the operation of the machine through use of keypads or alternatively imaging sensors of the type described. In this way users who wish to utilize hand movements to provide inputs may do so. An advantage of utilizing hand movements for providing machine inputs is that the user does not touch the keys of the keypad. This helps to avoid the risk of unauthorized persons intercepting the user's confidential PIN or other inputs. Further utilizing the imaging sensor to receive inputs also helps to reduce the risk that unauthorized persons can determine the type and amount of transaction that a blind user may be requesting at the automated banking machine. Additional benefits may be obtained depending on the particular type of transaction involved.

Figure 22:
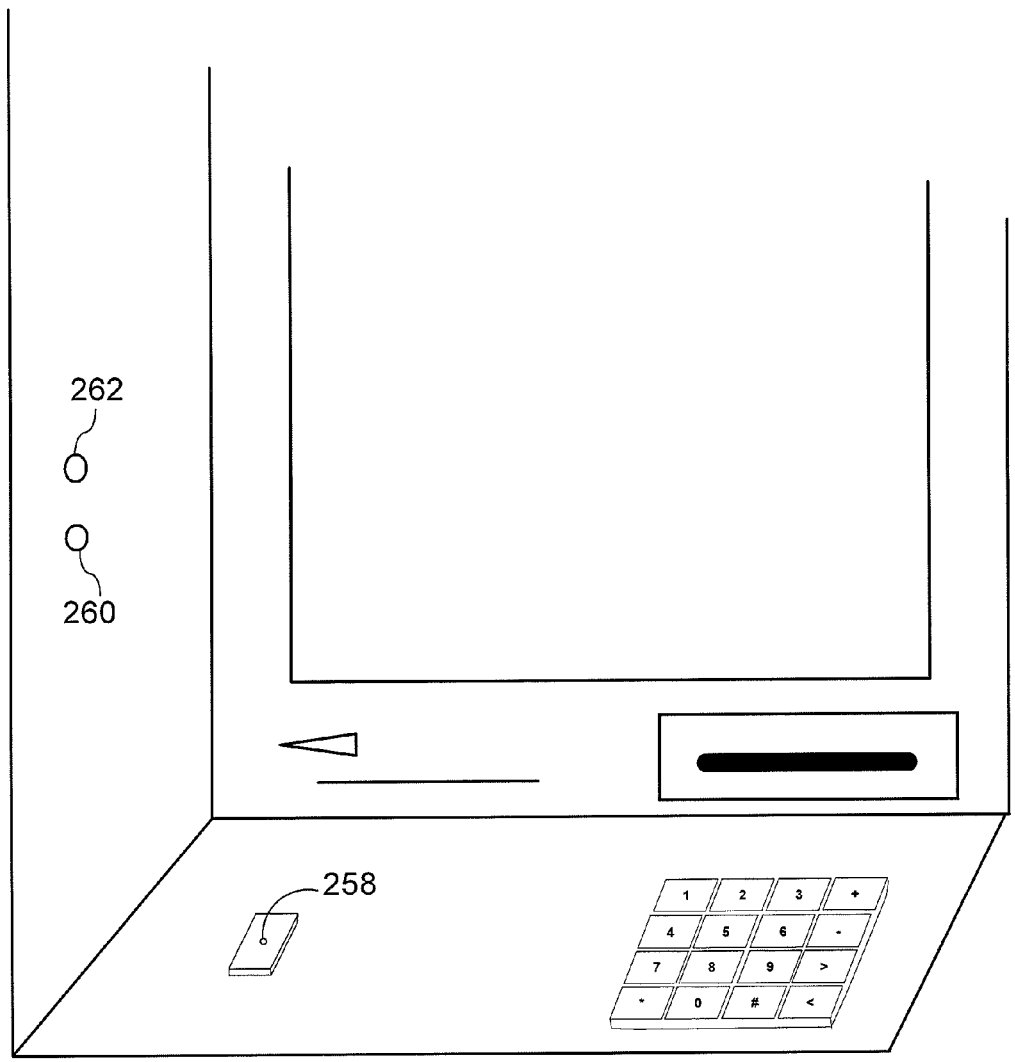

Other exemplary arrangements utilizing imaging sensors are represented by the alternative automated banking machine user interface represented in FIG. 22. In this alternative arrangement an imaging sensor 260 is positioned on a side surface which extends generally outward from the fascia of the automated banking machine. A speaker opening 262 is positioned adjacent to the imaging sensor 260. The speaker opening is associated with an audio speaker that produces outputs that can be perceived by a user by placing their ear in generally close proximity with the speaker opening.

This exemplary arrangement may be utilized to enable a user to operate the machine through voice guidance without the need for having a headphone connector. In this exemplary arrangement the user may place their ear in generally close relation with the speaker opening 262. Instructions provided responsive to operation of the controller may instruct the user to move their head in certain ways so as to provide inputs, select transaction types and to select amounts. By the user moving their head in the user desired manner, various inputs may be provided to the machine. In exemplary arrangements the user's ear may be positioned in generally close proximity to the speaker opening. The risk of interception of any of the audible outputs to the user may be reduced to the same level as would be achieved through the use of headphones. Further in this exemplary arrangement the user could avoid generally having contact with keys or other input devices of the machine in order to achieve operation.

Figure 23:
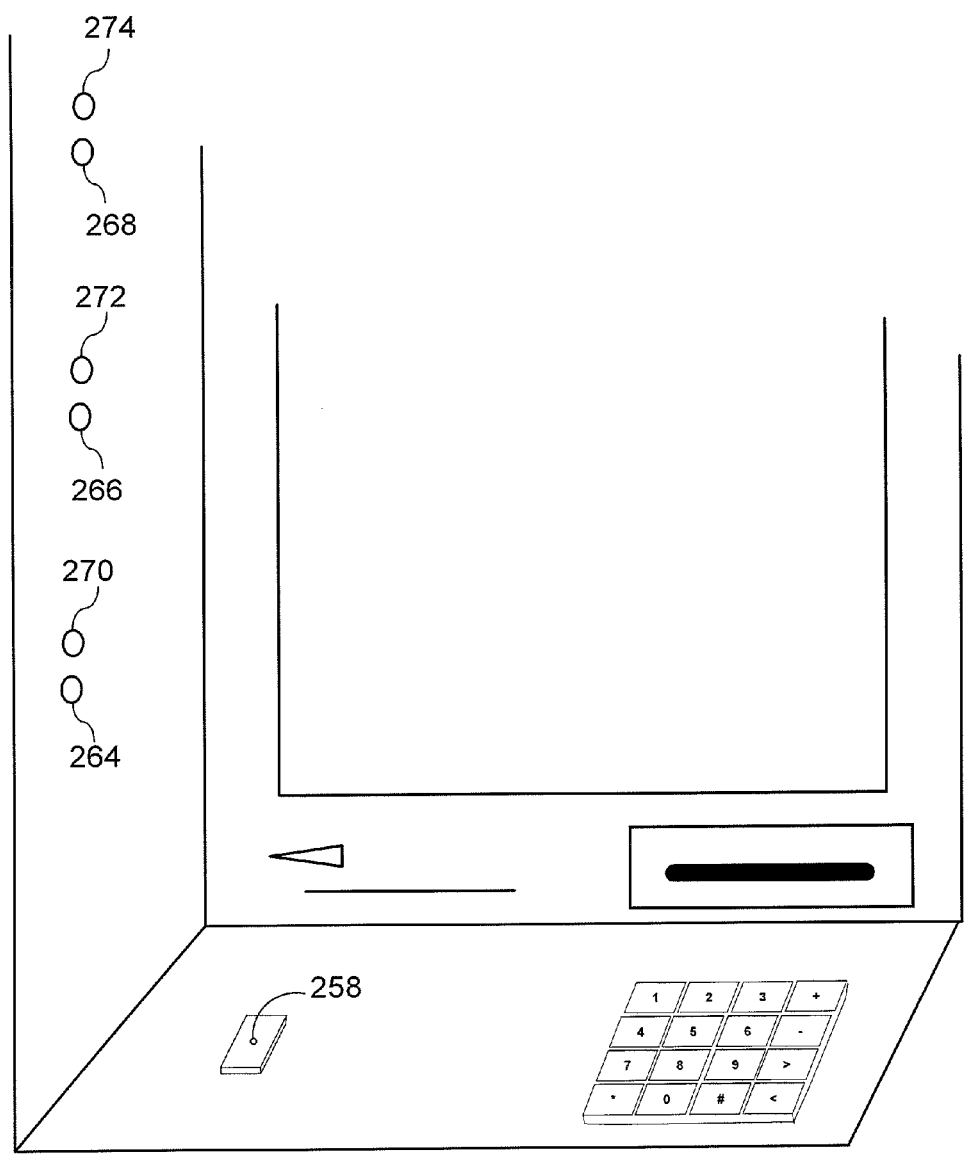

A further alternative arrangement is represented by the automated banking machine fascia shown in FIG. 23. In this exemplary arrangement three spaced imaging sensors 264, 266 and 268 are arranged in various positions of an outward vertically extending fascia wall of the machine. Each of the imaging sensors is associated with a respective adjacent speaker opening 270, 272 and 274.

As with the previously described arrangement this exemplary arrangement is configured to provide audible instructions through the speaker openings and to receive user inputs responsive to movement of the user's adjacent head or ear by an imaging sensor. In this exemplary arrangement by having multiple spaced imaging sensors and speaker openings, users of various stature may operate the machine by placing their head and ear adjacent to the sensor and speaker opening that is the most convenient for them. The exemplary controller may operate in accordance with its programming to sense the user's ear in proximity to the selected one of the imaging sensors and to provide the audible outputs through the associated speaker opening. In some exemplary arrangements the other speaker openings operate to provide masking sounds while the selected speaker opening is providing audible instructions so as to reduce the risk of unauthorized reception of instructions to the user. As with the other described arrangements the user may provide inputs including PIN data, transaction selection data, amounts and confirming inputs through movement in response to audible prompts that are generated through operation of the controller. Such a configuration may enable numerous different types of users to operate the machine in a suitable secure manner. Of course it should be understood that these arrangements of imaging sensors and audio output devices are exemplary and in other embodiments other approaches and arrangements may be used.

Thus the exemplary embodiments achieve improved operation, eliminate difficulties encountered in the use of prior devices and systems, and attain the useful results described herein.

In the foregoing description certain terms have been used for brevity, clarity and understanding. However, no unnecessary limitations are to be implied therefrom because such terms are used for descriptive purposes and are intended to be broadly construed. Moreover, the descriptions and illustrations herein are by way of examples and the invention is not limited to the features shown and described.

Further in the following claims any feature described as a means for performing a function shall be construed as encompassing any means known to those skilled in the art as being capable of carrying out the recited function and shall not be deemed limited to the particular means shown or described for performing the recited function in the foregoing description or mere equivalents thereof.

It should be understood that language which refers to a list of items such as "at least one of A, B, or C" (example 1) means "at least one of A, B and/or C." Likewise, it should be understood that language which refers to a list of items such as "at least one of A, B, and C" (example 2) means "at least one of A, B and/or C." The list of items in example 2 is not required to include one of each item. The lists of items in both examples 1 and 2 can mean "only one item from the list or any combination of items in the list." That is, the lists of items (in both examples 1 and 2) can mean only A, or only B, or only C, or any combination of A, B, and C (e.g., AB, AC, BC, or ABC).

The term "non-transitory" with regard to computer readable medium is intended to exclude only the subject matter of a transitory signal per se, where the medium itself is transitory. The term "non-transitory" is not intended to exclude any other form of computer readable media, including, but not limited to, media comprising data that is only temporarily stored or stored in a transitory fashion. Should the law change to allow computer readable medium itself to be transitory, then this exclusion is no longer valid or binding.

Having described the features, discoveries and principles of the exemplary embodiment, the manner in which it is constructed and operated and the advantages and useful results attained, the new and useful structures, devices, elements, arrangements, parts, combinations, systems, equipment, operations, methods, processes and relationships are set forth in the appended claims.

We claim:
1. Apparatus comprising:
  an automated banking machine configured to operate responsive at least in part to data read from data bearing records to cause financial transfers, including
    at least one of
      a card reader configured to read card data from user cards usable to identify financial accounts, and
      a wireless input device configured to receive mobile wireless data usable to identify user financial accounts from mobile wireless devices,
    a display,
    a cash dispenser, wherein the cash dispenser is configured to operate to selectively make cash stored within the machine accessible to users of the machine,
    at least one controller, wherein the at least one controller is configured to cause a determination to be made that either card data read from a user card or mobile wireless data received from a mobile wireless device corresponds to a financial account upon which a transaction is authorized to be conducted through operation of the machine, responsive at least in part to the determination, the cash dispenser to dispense cash, wherein the dispensed cash has an associated value, the financial account to be assessed an amount corresponding to the value, and wherein the at least one controller is configured to cause encrypted data corresponding to the financial account to be sent to at least one remote computer that does not have transaction authorization or denial capability, wherein the at least one remote computer is configured to calculate a number of transactions involving the financial account, and cause at least one alert message to be generated when the number exceeds a threshold.

2. The apparatus according to claim 1 wherein the at least one remote computer is configured to be incapable of determining an account number associated with the financial account from the encrypted data.

3. The apparatus according to claim 1 wherein the threshold corresponds to at least one of:
a total number of financial transactions involving the account within a time period,
a total number of financial transactions involving the account within a rolling time window, and
at least one time period between when financial transactions involving the account are conducted.

4. The apparatus according to claim 1
wherein the automated banking machine is configured to communicate with a remote host computer, wherein the at least one controller is operative to cause the cash dispenser to dispense cash responsive at least in part to communication with the remote host computer,
and wherein the at least one alert message is operative to cause the remote host computer to operate to cause the cash dispenser to not allow dispensing of cash.

5. Apparatus comprising:
an automated banking machine configured to operate responsive at least in part to data read from data bearing records to cause financial transfers, including
a reader configured to read data from data bearing items, and wherein the data is usable to identify an associated financial account,
a display,
at least one controller, wherein the at least one controller is operative to cause
a determination to be made responsive at least in part to communication with a remote transaction authorization capable host computer that data read from a data bearing item corresponds to a financial account on which a transaction is authorized to be conducted through operation of the machine,
responsive at least in part to the determination, the cash dispenser to make available to an operator of the machine, cash having an associated value,
the financial account to be assessed the associated value,
generation of encrypted data corresponding to the financial account,
the encrypted data to be sent to at least one remote computer other than the host computer, and wherein the at least one remote computer cannot determine the financial account from the encrypted data, and wherein the at least one remote computer is operative to receive encrypted data corresponding to the financial account from each of a plurality of automated banking machines when a transaction involving the financial account is conducted at a respective one of the automated banking machines, wherein the at least one remote computer is configured to:
calculate a number of transactions involving the financial account at the plurality of automated banking machines, and
cause at least one alert message to be generated when the number exceeds a threshold.

6. Apparatus comprising:
an automated banking machine configured to operate to cause financial transfers, including
at least one of
a card reader configured to read card data from user cards usable to identify financial accounts, and
a wireless input device configured to receive mobile wireless data usable to identify user financial accounts from mobile wireless devices,
a cash dispenser, wherein the cash dispenser is configured to operate to selectively make cash stored within the machine accessible to users of the machine,
at least one controller, wherein the at least one controller is configured to cause
a determination to be made that either card data read from a user card or mobile wireless data received from a mobile wireless device corresponds to a financial account upon which a transaction is authorized to be conducted through operation of the machine,
responsive at least in part to the determination, the cash dispenser to dispense cash, wherein the dispensed cash has an associated value,
the financial account to be assessed an amount corresponding to the value,
and wherein the at least one controller is configured to cause encrypted data corresponding to the financial account to be sent to at least one remote computer, wherein the at least one remote computer is not capable of determining an account number associated with the financial account from the encrypted data,
and wherein the at least one remote computer is configured to
calculate a number of transactions involving the financial account, and
cause at least one alert message to be generated when the number exceeds a threshold.

7. The apparatus according to claim 6
wherein the at least one remote computer is configured to calculate the number of transactions involving the financial account within a time window, and to cause the at least one alert message to be generated when the number within the time window exceeds the threshold.

8. The apparatus according to claim 7
wherein the encrypted data corresponds to a one-way hash of at least a portion of the card data.

9. The apparatus according to claim 7 wherein the at least one remote computer is in operative connection with a plurality of automated banking machines, and wherein the number corresponds to transactions involving the financial account at all of the plurality of automated banking machines.

10. The apparatus according to claim 6
wherein generation of the at least one alert message is operative to cause the at least one controller to not allow operation of the cash dispenser regardless of the card data corresponding to an account upon which a transaction is authorized to be conducted through operation of the machine.

11. Apparatus comprising:
an automated banking machine configured to operate to cause financial transfers, including
  a wireless input device configured to receive mobile wireless data usable to identify user financial accounts from mobile wireless devices,
  a display,
  a cash dispenser, wherein the cash dispenser is configured to operate to selectively make cash stored within the machine accessible to users of the machine,
  at least one controller, wherein the at least one controller is configured to cause
    a determination to be made that mobile wireless data received from a mobile wireless device through the wireless input device corresponds to a financial account upon which a transaction is authorized to be conducted through operation of the machine,
    responsive at least in part to the determination, the cash dispenser to dispense cash, wherein the dispensed cash has an associated value,
    the financial account to be assessed an amount corresponding to the value,
  wherein the at least one controller is configured to cause encrypted data corresponding to the financial account to be sent to at least one remote computer that does not have transaction authorization or denial capability, and wherein the mobile device is operative independent of the at least one controller to cause encrypted data corresponding to the financial account to be sent to the at least one remote computer,
  wherein the at least one remote computer is configured to calculate a number of transactions involving the financial account, and
    cause at least one alert message to be generated when the number exceeds a threshold.

12. The apparatus according to claim 11
wherein the at least one controller is configured to communicate with at least one host computer, wherein the at least one controller is operative to cause the cash dispenser to operate responsive at least in part to at least one communication received from the at least one host computer,
wherein the at least one remote computer receives the encrypted data corresponding to the financial account responsive to operation of the at least one host computer.

13. The apparatus according to claim 12 and further including the at least one remote computer,
wherein the at least one remote computer is configured to cause the at least one alert message to be sent to the at least one host computer, wherein the at least one host computer is operative responsive at least in part to the at least one alert message to cause denial of further requested financial transactions on the financial account that are received by the at least one host computer.

14. The apparatus according to claim 13
wherein the at least one remote computer is configured to be incapable of determining an account number associated with the financial account from the encrypted data.

15. The apparatus according to claim 14 and further including:
the at least one host computer,
wherein the at least one host computer includes at least one host computer data store, wherein the at least one host computer data store includes data corresponding to the encrypted data and data associated with the financial account,
wherein the at least one host computer is configured to operate responsive at least in part to the at least one alert message to determine the financial account corresponding to the encrypted data.

16. The apparatus according to claim 15
wherein the at least one host computer is operative responsive at least in part to the at least one alert message to send at least one denial message to the automated banking machine,
wherein the at least one controller is operative responsive at least in part to the at least one denial message to not enable the cash dispenser to dispense cash.

17. The apparatus according to claim 13
wherein the at least one remote computer is configured to
  receive encrypted data responsive to a mobile device operating to request a financial transaction corresponding to the financial account,
  cause at least one alternative alert message to be generated responsive to the at least one remote computer having not received either
    at least one message including the encrypted data responsive to operation of the mobile device, or
    at least one message including the encrypted data responsive to operation of the automated banking machine.

18. The apparatus according to claim 17
wherein the at least one controller is operative to not enable operation of the cash dispenser responsive at least in part to generation of the at least one alternative alert message.

19. Apparatus comprising:
at least one alerting computer configured to operate remotely from and in operative connection with a plurality of automated banking machines that are operative to cause financial transfers,
wherein each automated banking machine includes
  at least one of a reader or input device configured to receive account data usable to identify financial accounts,
  a display,
  at least one controller, wherein the at least one controller is operative to cause
    a determination to be made responsive at least in part to communication with a transaction authorization host computer which is other than the at least one alerting computer, that the account data corresponds to a financial account on which a transaction is authorized to be conducted through operation of the machine,
    responsive at least in part to the determination, the cash dispenser to make available to an operator of the machine, cash having an associated value,
    the financial account to be assessed the associated value,
    generation of encrypted data corresponding to the account data,
    the encrypted data to be sent to the at least one alerting computer,
wherein the at least one alerting computer is configured to
  be incapable of determining an account number associated with the financial account from the encrypted data,
  receive encrypted data corresponding to the account data from each of a plurality of automated banking machines when a transaction involving the financial account is conducted at a respective one of the plurality of automated banking machines, calculate a number of transactions involving the financial account at the plurality of automated banking machines from the encrypted data, and cause at least one alert message to be generated when the number exceeds a threshold.

20. The apparatus according to claim 19 wherein the at least one alerting computer is configured to receive encrypted data responsive to operation of a mobile device to request a transaction corresponding to the account independent of operation of any automated banking machine, cause at least one alternative message to be generated responsive at least in part to the at least one alerting computer having not received in connection with one transaction at a respective automated banking machine the encrypted data responsive to operation of the mobile device, or the encrypted data responsive to operation of the respective automated banking machine.

\* \* \* \* \*